US006526357B1

(12) United States Patent
Soussan et al.

(10) Patent No.: US 6,526,357 B1
(45) Date of Patent: Feb. 25, 2003

(54) ASSOCIATED PARAMETER MEASURING AND/OR MONITORING SUCH AS IN THE EVALUATION OF PRESSURE DIFFERENCES

(75) Inventors: Daniel A. Soussan, Lakewood, CO (US); Douglas P. Miller, Lakewood, CO (US)

(73) Assignee: Gambro, Inc., Lakewood, CO (US)

( * ) Notice: Subject to any disclaimer, the term of this patent is extended or adjusted under 35 U.S.C. 154(b) by 105 days.

(21) Appl. No.: 09/631,204

(22) Filed: Aug. 1, 2000

Related U.S. Application Data

(60) Provisional application No. 60/147,958, filed on Aug. 9, 1999.

(51) Int. Cl.$^7$ .............................................. G06F 19/00
(52) U.S. Cl. ........................................... 702/45; 702/100
(58) Field of Search ..................... 604/65; 364/509; 702/45; 73/304; 222/15

(56) References Cited

U.S. PATENT DOCUMENTS

| | | |
|---|---|---|
| 3,946,731 A | 3/1976 | Lichtenstein |
| 4,083,777 A | 4/1978 | Hutchisson |
| 4,161,880 A | 7/1979 | Prosky |
| 4,168,517 A | 9/1979 | Lee |
| 4,227,420 A | 10/1980 | Lamadrid |
| 4,315,309 A | 2/1982 | Coli |
| 4,370,983 A | 2/1983 | Lichtenstein |
| 4,403,296 A | 9/1983 | Prosky |
| 4,600,401 A | 7/1986 | Kamen |
| 4,661,246 A | 4/1987 | Ash |
| 4,710,164 A | 12/1987 | Levin et al. |
| 4,718,891 A | 1/1988 | Lipps |
| 4,739,492 A | 4/1988 | Cochran |
| 4,828,543 A | 5/1989 | Weiss et al. |
| 4,879,040 A | 11/1989 | Prince et al. |
| 4,954,128 A | 9/1990 | Ford |
| 5,069,792 A | 12/1991 | Prince et al. |
| 5,174,894 A | 12/1992 | Ohsawa et al. |
| 5,200,090 A | 4/1993 | Ford et al. |
| 5,211,849 A | 5/1993 | Kitaevich et al. |
| 5,234,608 A | 8/1993 | Duff |

(List continued on next page.)

FOREIGN PATENT DOCUMENTS

| | | |
|---|---|---|
| EP | 0967554 A1 | 12/1999 |
| EP | 0990417 A1 | 4/2000 |
| EP | 0990418 A1 | 4/2000 |
| EP | 0992215 A1 | 4/2000 |
| EP | 0993803 A1 | 4/2000 |
| EP | 0997102 A1 | 5/2000 |
| EP | 0997103 A1 | 5/2000 |

Primary Examiner—John S. Hilten
Assistant Examiner—Xiuqin Sun
(74) Attorney, Agent, or Firm—Peter H. Scull; Edna M. O'Connor; Laura M. Butterfield

(57) ABSTRACT

Correction quantities are generated for yielding closer approximations of actual parameters. These are obtained by preliminarily subjecting parametric transducers to preselected parametric values and recording the measured values for each transducer in a data table for later use as or in correction quantities. An embodiment includes interpolation relative to data table values closest to the operationally measured parametric value and using the resulting interpolated value as a corrected parametric value. Such interpolations may be performed for two parametric transducers relative to two substances. The resulting corrected parametric values may then be subtracted to obtain a parametric difference. A further embodiment may include using correction quantities of a reference parametric transducer in interpolation calculations for the actual parametric transducers. Similarly, other data table correction recordations such as differences between two measured parameters can be used to modify an operationally measured parametric differential. Reference transducer corrections can be used here as well.

22 Claims, 7 Drawing Sheets

U.S. PATENT DOCUMENTS

| | | |
|---|---|---|
| 5,263,924 A | 11/1993 | Mathewson |
| 5,277,188 A | 1/1994 | Selker |
| 5,326,476 A | 7/1994 | Grogan et al. |
| 5,344,568 A | 9/1994 | Kitaevich et al. |
| 5,370,123 A | 12/1994 | Shinzato |
| 5,372,709 A | 12/1994 | Hood |
| 5,431,811 A | 7/1995 | Tusini et al. |
| 5,441,636 A | 8/1995 | Chevallet et al. |
| 5,473,537 A | 12/1995 | Glazer et al. |
| 5,482,049 A | 1/1996 | Addiss et al. |
| 5,487,827 A | 1/1996 | Peterson et al. |
| 5,497,665 A | 3/1996 | Cage et al. |
| 5,510,716 A | 4/1996 | Buffaloe, IV et al. |
| 5,510,717 A | 4/1996 | Buffaloe, IV et al. |
| 5,536,237 A | 7/1996 | Prince et al. |
| 5,551,440 A | 9/1996 | Miyawaki |
| 5,618,441 A | 4/1997 | Rosa et al. |
| 5,645,642 A | 7/1997 | Nishizato et al. |
| 5,650,071 A | 7/1997 | Brugger et al. |
| 5,690,831 A | 11/1997 | Kenley et al. |
| 5,706,661 A | 1/1998 | Frank |
| 5,711,302 A | 1/1998 | Lampropoulos et al. |
| 5,711,883 A | 1/1998 | Folden et al. |
| 5,725,776 A | 3/1998 | Kenley et al. |
| 5,745,377 A * | 4/1998 | Power et al. ............... 364/509 |
| 5,749,364 A | 5/1998 | Sliwa, Jr. et al. |
| 5,776,091 A | 7/1998 | Brugger et al. |
| 5,788,851 A | 8/1998 | Kenley et al. |
| 5,910,252 A | 6/1999 | Truitt et al. |
| 6,045,510 A | 4/2000 | Ogura et al. |
| 6,280,408 B1 * | 8/2001 | Sipin ......................... 604/65 |

* cited by examiner

US 6,526,357 B1

ASSOCIATED PARAMETER MEASURING AND/OR MONITORING SUCH AS IN THE EVALUATION OF PRESSURE DIFFERENCES

This patent document claims the benefit of the U.S. Provisional Application having the Ser. No. 60/147,958; filed on Aug. 9, 1999.

FIELD OF THE INVENTION

The present invention generally involves means and methods for measuring and/or monitoring parametric differences between associated fluid materials and is more particularly directed to measuring a pressure difference between fluids separated by a semi-permeable membrane. Pressure difference monitoring according to this invention presents a distinct advantage in extracorporeal blood systems, particularly in a procedure called therapeutic plasma exchange (TPE).

BACKGROUND OF THE INVENTION

Many fluid systems require accurate measurements of various properties and/or parameters of the fluids flowing therethrough. In some of these systems, the importance derives from the measurements of individual parameters. In other cases, it is the change or difference in parameters that is important. In either event, the accuracy required for each particular fluid system may vary according to the particular fluid(s) involved and/or depending on the purpose of that system.

An example of a fluid system having special requirements which can be significantly impacted by the accuracy of parametric measurements, particularly involving pressure determinations, is a blood flow system outside the body, also known as an extracorporeal blood system. An extracorporeal blood system usually includes a device for processing the blood flowing therethrough. There are numerous types of such devices. Filtration devices having semi-permeable membranes are commonly used in extracorporeal blood systems such as those used in dialysis or therapeutic plasma exchange (TPE). The primary purpose of a semi-permeable membrane is usually to provide for the removal or separation of certain elements or components from the blood. Urea and other waste products are removed from blood in dialysis, and blood plasma is separated from the red blood cells in TPE. The processed blood or red blood cells are then returned to the patient.

More specifically, in an extracorporeal blood system using a semi-permeable membrane device, the process is as follows. Blood is removed from the patient, passed along and in contact with one side of a semi-permeable membrane. Unwanted portions of the blood (urea in dialysis, plasma in TPE) diffuse or filter through the pores of the semi-permeable membrane. The blood remaining on the blood side of the semi-permeable membrane is then returned to the patient with less of the unwanted substance.

Poor accuracy of pressure measurements in this art can create problems for the blood cells flowing through such a system. Excessive pressures or pressure differentials may cause red blood cells to become stuck in certain components of the system such as in the pores of a semi-permeable membrane and/or, at worst, these red cells may be pushed into or against certain system components until the red cells burst, a consequence called hemolysis. Repetitive red cell destruction in this fashion would then result in a reduction in the number of red blood cells available for carrying oxygen to the other cells of the body. A substantial reduction in red blood cells can thereby lead to oxygen deficiency injury or death. On the other hand, insufficient pressure differences in extracorporeal blood systems will result in less effective separation of the blood components from each other, as for example, of urea from the blood in a dialysis system, or of red blood cells from plasma in apheresis or therapeutic plasma exchange (TPE).

The performance of semi-permeable membrane systems, and indeed of the membranes themselves, depends, in part, on the pressure difference across the membrane which is called the trans-membrane pressure (TMP). Generally, as the TMP across the membrane increases, more unwanted substances pass through it. If the TMP on the membrane is large enough, the membrane will rupture or the blood will be damaged as described above. Therefore, there is often a desire to make the TMP as high as possible to make the treatment proceed faster, but not so high as to damage the membrane or the blood. The more accurately the TMP can be measured, the closer to the damage point the treatment can be performed.

Pressure difference monitoring across a semi-permeable membrane has been conventionally performed using two pressure transducers in the fluid system, one on each side of the membrane. Pressure readings are then taken and, either manually or using a microprocessor, one measured pressure is subtracted from the other. The resulting pressure difference is the trans-membrane pressure (TMP) referred to above. Also, because the fluid pressure varies along the length of the membrane, additional pressure transducers have also been used on either or both sides of a membrane to improve the accuracy of the ultimate TMP calculation. Average pressures on either or each side of the membrane can thus be obtained and these resulting average pressures subtracted one from the other to yield a better approximation of the actual pressure difference across the membrane.

More particularly, in conventional extracorporeal blood systems using a semi-permeable membrane disposed inside a filter device, it is common to measure the pressures outside, yet near the filter device with pressure transducers disposed adjacent the inlet and outlet of the filter device on the blood side of the membrane and adjacent the outlet of the filtrate side of the membrane. This allows calculation of an average TMP with the formula:

$$\text{Average TMP} = \frac{\text{Blood Inlet} + \text{Blood Outlet}}{2} - \text{Filtrate Outlet}$$

On the other hand, the maximum TMP experienced by the membrane needs only two of these transducer readings; namely, the pressure measurement at the blood inlet to the filter device and the measurement at the filtrate outlet. Thus, this maximum TMP maybe expressed as:

Maximum TMP=Blood Inlet−Filtrate Outlet.

Thus, using three pressure transducers, one each at the blood inlet, blood outlet and filtrate outlet, both the average and maximum TMP's can be calculated. Note, the semi-permeable membrane performance is generally associated with the average TMP, whereas failure of the membrane is usually related to the highest TMP experienced by the membrane.

Nonetheless, both of these (and all other conventional) methods also depend for accuracy upon the precision of the transducers used. And, most measuring systems have some inherent inaccuracy associated with them. Indeed, pressure transducers in this field commonly exhibit ±10% error in accuracy each relative to the actual pressure at that respective point in the fluid system. A linearity error of ±1% can also be expected. When using two or more of such transducers to determine a pressure difference, these error margins can then be compounded.

For example, in a typical pressure transducer system for an extracorporeal blood system which has an inaccuracy of ±10% for each transducer measurement, the overall accuracy of the pressure difference when measured with a two transducer system may be reduced by as much as a first ±10% from the first measurement. And, it may experience a still further accuracy reduction of an additional ±10% from the second measurement. This invention is intended to address this compounding of measurement error.

It is further apparent that there remains a distinct need for continued improvements in parametric monitoring particularly in fluid pressure difference evaluation which provides for more accurately determining the difference between the pressures occurring on both sides of a semi-permeable membrane. Better accuracy in pressure difference measurements will provide better achievement of target pressure differences in practice to substantially eliminate hemolysis and improve fluid component separation. It is toward all of these ends that the present invention is directed.

SUMMARY OF THE INVENTION

The present invention is directed to means and methods for approximating pressure differentials experienced in a fluid system. More particularly, the present invention involves using preliminarily measured and/or calculated correction quantities to modify the operationally measured pressure values to arrive at a closer approximation of the actual pressure differential.

In general, the correction quantities used herein are obtained by preliminarily pressurizing the system pressure transducers to various pre-selected pressures and recording the corresponding preliminarily measured values for each transducer in a data table for later use as or in the derivation of correction quantities. A first use of such correction quantities is to interpolate between the two closest data table values relative to the operationally measured pressure value and use the resulting interpolated value as the corrected pressure value. This sort of interpolation may be performed for each of two pressure transducers, one on each side of the membrane. The resulting corrected pressure values are then subtracted from each other to obtain the corrected pressure difference or TMP. An alternative of this correction scheme involves using data table correction quantities of a reference pressure transducer in the interpolation calculations of the two membrane pressure transducers.

Similarly, other correction quantities can be recorded in a data table during a preliminary pressurization phase as describe briefly above. For example, the respective differences between the two preliminarily measured pressures of each of the trans-membrane pressure transducers may be recorded as correction quantities for each preliminarily applied pressurization. These correction quantities can then be used to mathematically modify the operationally measured pressure differential during actual fluid flowing use. Also, a reference transducer can be used here as well such that the differences between one membrane transducer and the reference transducer can be recorded in the data table as one set of correction quantities, and the differences between the other membrane transducer and the reference can be recorded as a second set of correction quantities. Both correction quantities may then be used in the ultimate determination of the pressure difference across the membrane, the TMP.

Other fluid parameters such as temperature, volume, flowrate and the like can also be better evaluated according to the present invention. For the purposes hereof, fluids include gases and/or liquids.

Accordingly, the primary object of the present invention is to provide improved accuracy in determining the parameters exhibited in a fluid system, particularly in determining pressure differentials in fluid systems having two or more fluids separated by a membrane.

A further object is to improve pressure differential accuracy using only two pressure transducers; one on each side of a membrane.

A still further object is to improve pressure differential accuracy using two pressure transducers; one on each side of a membrane both modified relative to a third pressure transducer.

These and other features of the present invention will be further illuminated in the following detailed description read in conjunction with the accompanying drawings which are described briefly below.

DETAILED DESCRIPTION

Figure 1:
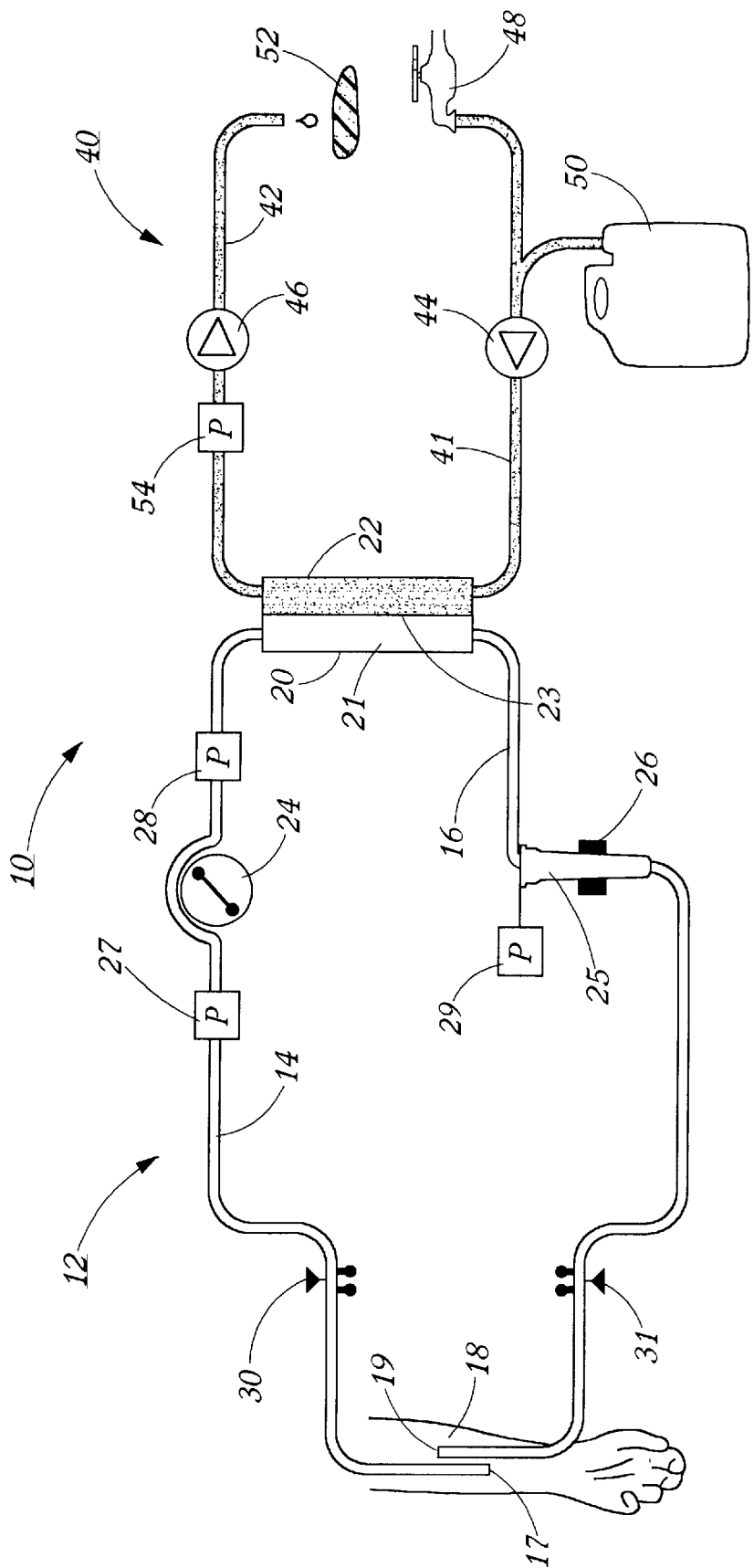
FIG. 1 is a schematic view of an extracorporeal fluid system in which the pressure monitoring means and methods of the present invention may be used.

The present invention is primarily directed to means and methods for measuring pressure differentials, an exemplary use of which is shown in the attached drawings. As discussed below, this invention can be used in numerous fluid systems. Use in one preferred system, generally referred to as dialysis, will now be described. The general term dialysis as used here includes hemodialysis, hemofiltration, hemodiafiltration and therapeutic plasma exchange, among other similar treatment procedures. In dialysis generally, blood is taken out of the body and exposed to a treatment device to separate substances therefrom and/or to add substances thereto, and is then returned to the body.

An extracorporeal blood treatment system capable of performing general dialysis (as defined above, including TPE) is shown and identified in the attached drawings by the reference numeral 10. In particular and as shown primarily in FIG. 1, system 10 generally comprises a blood tubing circuit 12 having first and second tubing segments 14 and 16 which are both connected to the vascular system of a patient 18 via access and return devices 17 and 19, respectively. Devices 17 and 19 are preferably cannulas, catheters, winged needles or the like as understood in the art. Tubing segments 14 and 16 are also connected to a filtration or processing unit 20. In dialysis, filtration unit 20 is a dialyzer, which is also often referred to as a filter. In TPE, it may also be referred to as a plasma filter. Filtration unit 20 is shown schematically divided into a primary chamber 21 separated from a secondary chamber 22 by a semi-permeable membrane 23 (not shown in detail). In this extracorporeal system 10, primary chamber 21 accepts blood flow from blood circuit 12 and, as described below, processing fluid flows in and through secondary chamber 22. A peristaltic pump 24 is disposed in operative association with the first tubing segment 14 and an air bubble trapping drip chamber 25 is shown in the second tubing segment 16. A bubble detector 26 is often included on or adjacent the bubble trap 25. Numerous other component devices of blood circuit 12 are preferably also included as, for example, the three pressure sensors 27, 28, and 29 as well as the tubing clamps 30 and 31.

Also shown schematically in FIG. 1 is the processing fluid or filtrate side of system 10 which generally comprises a processing fluid circuit 40 having first and second processing fluid tubing segments 41 and 42. As mentioned, each of these tubing segments is connected to the secondary chamber 22 of filtration unit 20. In this schematic, a respective fluid pump 44, 46 is operatively associated with each of these tubing segments 41 and 42. First tubing segment 41 is also connected to a processing fluid source 48 which may include electrolytes pre-mixed therein or which may be added by an online source 50 (or multiple sources, not shown). In dialysis, the processing fluid is a dialysate mixture preferably including sodium bicarbonate, inter alia, as is known in the art. A fluid bag 49 (or bags) (see FIGS. 2 and 3, below) may be used in lieu of sources 48 and 50. Dry powder canisters (not shown) may also be used as is known in the art. Second tubing segment 42 is connected to a waste collection device which, as shown schematically in FIG. 1 could be a drain 52. The waste device is also commonly a waste container such as a bag 53 (not shown in FIG. 1, but see description relative to FIGS. 2 and 3, below). A pressure sensor 54 is also disposed in second dialysis fluid tubing segment 42. At times in TPE and certain other dialysis procedures, no processing fluid is added or pumped into the system. Rather, only filtrate may be removed through the membrane 23 and pumped out of the filtration device 20 through tubing segment 42.

Figure 2:
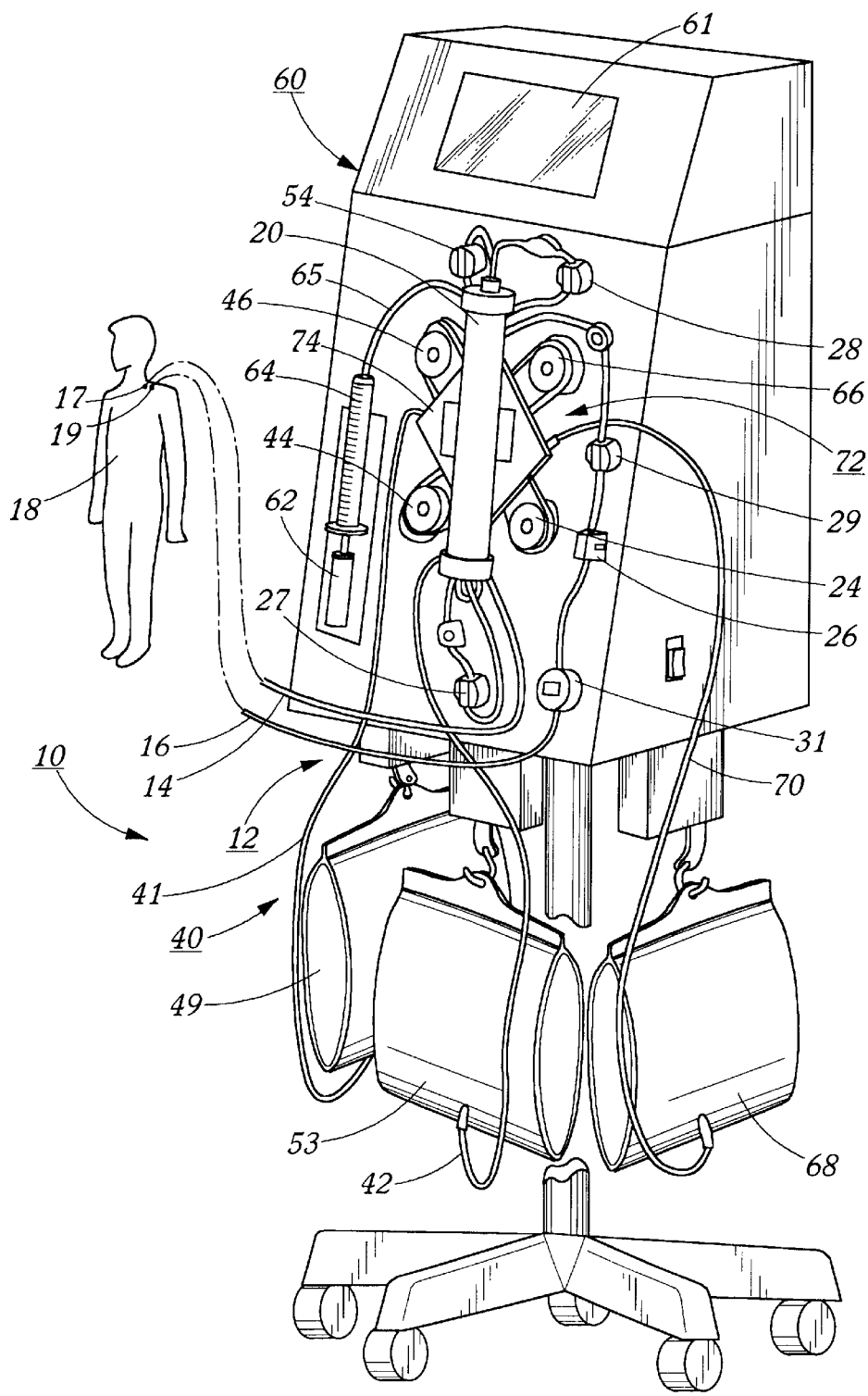
FIG. 2 is an isometric view of an extracorporeal fluid apparatus generally incorporating an extracorporeal system such as that shown in the schematic of FIG. 1.
Figure 3:
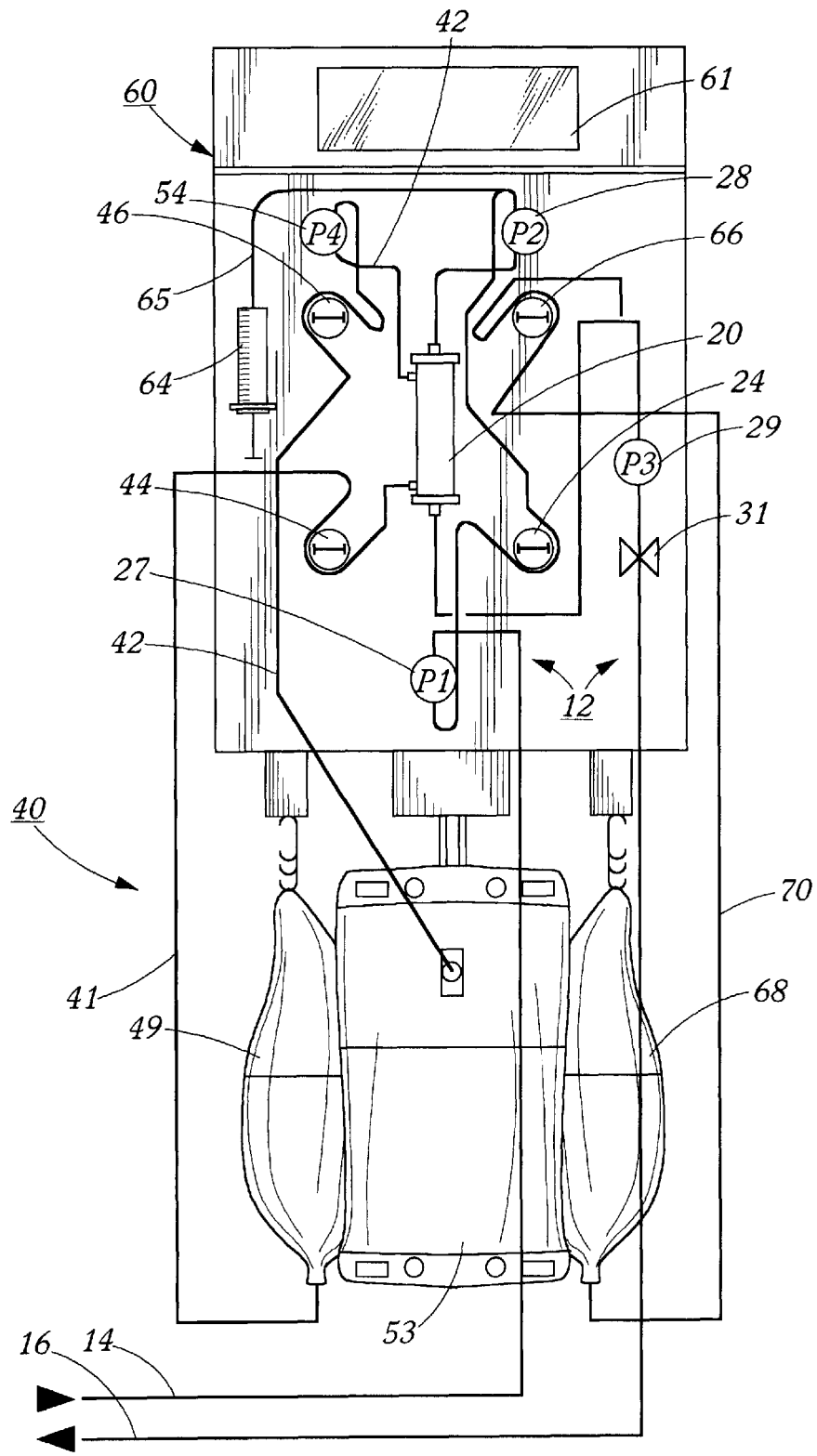
FIG. 3 is a schematic view of a fluid system like that shown in FIG. 1 as incorporated on the extracorporeal apparatus of FIG. 2.

FIG. 1 shows and the above description describes a system which is common as a basic model for numerous dialysis procedures including TPE. Additional fluid lines, circuits, and componentry may be added (or deleted) to increase treatment options. Shown in more detail in FIGS. 2 and 3 is an apparatus 60 which may be used to provide the basic fluid circuits shown in FIG. 1 as well as some additional features with which the present invention may be used. Though less complex apparatuses may be available for use with the present invention, it is preferred to be employed with an apparatus such as apparatus 60 as described and shown herein. In particular, FIGS. 2 and 3 depict an extracorporeal blood processing or dialysis apparatus 60 which provides numerous treatment options which are controlled and/or monitored via the control/display screen 61. Touch-screen controls may be incorporated herewith and/or other conventional knobs or buttons (not shown) may be used. Other and more detailed information regarding an example apparatus 60 may be found in U.S. Pat. Nos. 5,679,245; 5,762,805; 5,776,345 and 5,910,252; inter alia.

A general dialysis treatment procedure as performed, for example, with an apparatus 60, will now be described with reference to FIGS. 2 and 3. First, blood is removed from the patient 18 via access device 17 and flows through access line 14 to the apparatus 60 and filter 20. Apparatus 60 and filter 20 process this blood according to a selected one or more of a number of extracorporeal blood treatment protocols and then return the processed or treated blood to the patient 18 through return line 16 and return device 19 inserted in or otherwise connected to the vascular system of the patient 18. The blood flow path to and from the patient 18, which includes the access device 17, the access line 14, the filter 20, as well as the return line 16 and return device 19 back to the patient forms the blood flow circuit 12 such as the schematic one shown and described relative to FIG. 1 above.

Each of the treatment protocols used by apparatus 60 preferably involves passing the blood in the blood circuit 12 through filtration unit 20. The filtration unit 20 uses a conventional semi-permeable membrane (not specifically shown in FIGS. 2 and 3) which, as described above, divides the filter 20 into primary and secondary chambers 21 and 22 (also not specifically shown in FIGS. 2 and 3). The semi-permeable membrane confines the blood in the primary circuit 12 to the primary chamber 21. The semi-permeable membrane allows matter or molecules from the blood in the primary chamber 21 to migrate (by diffusion or convection) across the semi-permeable membrane into the secondary chamber 22, and generally may also allow matter or molecules from the secondary chamber to diffuse across the semi-permeable membrane from secondary chamber 22 into the blood in the primary chamber 21. Each treatment protocol here generally involves removing extracorporeally undesired matter from the blood and/or adding extracorporeally desirable matter to the blood.

First pressure sensor 27 is shown in FIGS. 2 and 3 as it is connected in the access line 14 (this connection is shown better in FIG. 3). The first pressure sensor 27 allows the fluid pressure in the access line 14 to be monitored independently as well as being used in measuring the trans-membrane pressure (TMP) as is described below.

The first peristaltic pump 24 is also shown as operably connected to the access line 14 and controls the rate of blood flow through the blood circuit 12. Typically, the first pump 24 is operated when the blood to be treated is withdrawn from an artery or vein of the patient 18 through access device 17. The first pump 24 creates a pressure downstream thereof in the access line 14 which is higher than the blood pressure in the patient's return blood vessel in which the return device 19 is inserted. The pressure differential created by the first pump 24 draws the blood from the vascular blood source through the access device 17, and forces it through the blood circuit 12, the filtration unit 20 and back through the return line 16 and return device 19 into the lower pressure environment of the patient's return blood vessel.

Second pressure sensor 28 is connected in the blood circuit 12 between the first pump 24 and the blood entrance into the filter 20. Besides being used for calculation of the TMP as described hereinbelow, another general function of the second pressure sensor 28 is to detect and monitor the pressure of the blood supplied to the entrance to the filter 20.

This information may be used to indicate an alarm, for example, if the blood pressure at the entrance falls below a predetermined value, in which case blood may be leaking.

A third pressure sensor 29 is connected at or near the outlet of the filter 20. Here also, a featured purpose of sensor 29 is in the determination of the TMP; however, another of its functions is to monitor the pressure of the blood in the return line 16 at the exit from the filter 20 for comparison with the pressure sensed by the sensor 28 such that the integrity of the flow path through the filter 20 can be monitored and, in particular, clotting of blood inside filter 20 can be detected. In addition, if the return pressure detected by the third pressure sensor 29 is below a pre-selected level, disconnection of the return line 16 or the return device 19 may be indicated.

A bubble detector 26 is shown in FIG. 2 as preferably connected in the blood circuit 12 on apparatus 60 downstream of the third pressure sensor 29. The bubble detector 26 is one of many known in the art and its function is to detect the possible presence of bubbles and microbubbles in the treated blood being returned to the patient 18 in the return line 16. A bubble trap 25 is not shown in FIGS. 2 or 3. This illustrates a concept known in the art that a bubble trap is not required though it had customarily been preferred in these procedures as shown in the embodiment of FIG. 1.

Downstream of bubble detector 26, a return clamp 31 is also shown as preferably connected in the blood circuit 12. Return clamp 31 selectively allows or terminates the flow of blood through the blood circuit 12. Preferably, return clamp 31 may be activated whenever air is detected in the blood by bubble detector 26.

It is desirable when performing any of the various extracorporeal treatments possible using the apparatus 60 that anticoagulant be added to the blood in the blood circuit 12. The anticoagulant is preferably added to the blood prior to its delivery to the filter 20 in order to prevent undesirable coagulation of the blood resulting from contact of the blood with the semi-permeable membrane and/or other components within the blood circuit 12. To add the anticoagulant, a pump 62 (see FIG. 2) on apparatus 60 is connected to an anticoagulant container 64 to deliver anticoagulant through an anticoagulant line 65 to the blood in tubing segment 14. The anticoagulant container 64 is preferably a conventional syringe having a barrel and a plunger, and the pump 62 is a mechanical drive device to move the plunger into the barrel, thereby dispensing the anticoagulant into the blood in the blood circuit 12 on either a continuous or periodic basis. The anticoagulant container may also be a container connected to scales which weigh the content of the anticoagulant in the anticoagulant container. In such a case (not shown), pump 62 would preferably be a peristaltic pump (also not shown) which would deliver the anticoagulant from the anticoagulant container through the anticoagulant line 65.

It is sometimes desirable when performing certain treatments using the apparatus 60, such as in TPE procedures, to add a replacement fluid to the blood flowing in the blood circuit 12. The replacement fluid adds material to the blood in order to adjust the pH of the blood, to add nutrients to the blood, or to add fluid to the blood (as in TPE), among other options known in the art. A second peristaltic pump 66 is connectable to the blood circuit 12 either before the entrance of the blood into the filtration unit 20 (not shown), or as shown in FIG. 3, after the exit of the blood from the filter 20. The second pump 66 delivers the replacement fluid from a replacement fluid container or bag 68 through a replacement fluid line 70.

The secondary flow circuit 40 is also shown in FIGS. 2 and 3 as it interacts with apparatus 60 and filter 20. The secondary flow circuit 40 is connected to the secondary chamber 22 (see FIG. 1) of filter 20. Matter extracorporeally removed from the blood is removed from the secondary chamber 22 of filter 20 through the outlet tubing segment 42 of the secondary flow circuit 40, and matter extracorporeally added to the blood is moved into filter 20 through inlet tubing segment 41 of the secondary flow circuit 40. The secondary flow circuit 40 generally includes a fluid source such as bag 49, inlet fluid line 41, third peristaltic pump 44, the secondary chamber 22, a waste fluid line 42, fourth pressure sensor 54, fourth pump 46, and a waste collection device such as container 53. As is understood, in some extracorporeal blood treatment protocols, discrete mechanical components of the secondary flow circuit 40 may not be used and/or required.

The source fluid bag 49 contains a sterile processing fluid, generally isotonic to blood, into which blood impurities will diffuse through the semi-permeable membrane of the filtration unit 20. The pump 44 is connected in inlet fluid line 41 for delivering processing fluid from the processing fluid source 49 into an entrance to the filter 20.

The waste collection container 53 is provided to collect or receive matter from the blood transferred across the semi-permeable membrane in filter 20 and/or to receive the used processing fluid after it has passed through the filter 20. The fourth pump 46 is connected to the waste collection line 42 for moving body fluid from the filter 20 into the waste collection container 53. The fourth pressure sensor 54 is also located in the waste collection line 42 for the primary purpose of monitoring the pressure in the secondary chamber 22 of filter 20. In the present invention, this pressure value is used with the pressure values obtained from pressure sensor 28 and/or pressure sensors 28 and 29 to calculate the trans-membrane pressure (TMP) with better accuracy as will be described below. Plugging of the pores of the semi-permeable membrane can also be detected by monitoring the average pressure upstream and downstream of the filter 20 as sensed by second and third pressure sensors 28 and 29, the pressure in the collection line 42 as sensed by fourth pressure sensor 54 and the actual flow rate of the collection fluid.

Preferably, the filtration unit 20, the flow tubing lines, and the other components in the primary and secondary flow circuits 12 and 40 described herein (with the exception of the pumps and a few other items as is now apparent or as will be described) are formed as an integral, replaceable unit. An example of such an integral replaceable unit is described in greater detail in U.S. Pat. No. 5,441,636 entitled Integrated Blood Treatment Fluid Module (see also, U.S. Pat. No. 5,679,245, entitled Retention Device for Extracorporeal Treatment Apparatus). As is described in greater detail therein and as can generally be appreciated from FIGS. 2 and 3, the integrated tubing and filter module (identified in FIG. 2 by the reference numeral 72) comprises the filter 20 and all the tubing and related componentry described above which is connectable to control apparatus 60. The filter and tubing are retained on a plastic support member 74 which is, in turn, connectable to apparatus 60. When in the operative position connected to apparatus 60, flexible fluid conducting tubing lines to and from the filtration unit 20 are held in operative, pump communicative loops for operative contact with the peristaltic pumping members of the pumps 24, 44, 46 and 66 to cause the fluid to flow through the primary (blood) and secondary (processing fluid) circuits 12 and 40. Module 72, including filter 20 and all the tubing lines and associated flow componentry are preferably disposable after use. The peristaltic pumping members of pumps 24, 44, 46, and 66 as fixedly disposed on apparatus 60 (without the disposable tubing loop components) are re-usable. In general, the electrical or electromechanical components are also fixedly disposed in or on apparatus 60. Examples of these include the display screen 61, the bubble detector 26, line clamps 30 and 31 and the transducer portions of sensors 27, 28, 29 and 54 as will be described below.

Due to various portions of the fluid circuits being hidden by support member 74 of module 72 in FIG. 2, the fluid circuitry used on the apparatus 60 is shown in more detail in FIG. 3. The blood circuit 12 is shown schematically beginning at the lower portion of FIG. 3 with the first tubing segment 14 providing for blood flow from the patient to the blood processing apparatus 60 and the second tubing segment 16 carrying processed blood back to the patient. When blood from the patient reaches the processing apparatus 60, it first flows through first pressure sensor 27 (P1). The blood then travels through pump 24 and through second pressure sensor 28 (P2) on its way to filter 20. Note, FIG. 3 shows the addition of anticoagulant (e.g., heparin) injected in tubing segment 14 between pump 24 and pressure sensor 28. Anticoagulant may be injected at many potential locations in the blood circuit 12 as understood in the art; thus, though preferred, this location is merely illustrative.

After passing through the second pressure sensor 28, the blood then flows into the blood processing or filtration unit 20. Entering flow is shown here at the top of unit 20. Exit flow of processed blood is then shown at the bottom of unit 20. The exiting processed blood then travels to and through the third pressure sensor 29 (P3), line clamp 31 and back to the patient through tubing segment 16. Note here again, a bubble trap 25 is not shown although it could be used as is known in the art. Bubble sensor 26 is similarly not shown. Tubing line clamp 30 is also not shown although at least a return clamp 31 is preferably provided prior to return to the patient. Also shown in FIG. 3 relative to blood circuit 12 is the optional addition of a substitution fluid into the processed blood prior to its return to the patient. Substitution fluid may be added either before or after flow through the filtration unit 20 or at numerous other points in the blood flow circuit as is also known in the art. In FIG. 3, substitution fluid is shown being added after processing in filter 20. Here, substitution fluid is contained in a bag 68 and pumped through a line 70 by pump 66 into tubing segment 16 flowing back to the patient.

The dialysate or processing fluid circuit 40 is also shown in better detail in FIG. 3. The processing fluid shown in FIG. 3 is pre-mixed and held in a bag 49 (which substitutes for the fluid and electrolyte sources 48 and 50 shown and described relative to FIG. 1). Processing fluid is pumped through tubing segment 41 via pump 44 to the processing unit 20. The processing fluid collects waste products from the blood in processing unit 20 and then emerges to flow to the effluent or waste bag 53 (which corresponds to the drain device 52 shown and described relative to FIG. 1). Note, the words effluent and waste are intended to be substantially synonymous and are used interchangeably herein. This effluent or waste processing fluid first flows through the fourth pressure sensor 54 (P4) and through pump 46 on its way to the waste bag 53. Again, as is known in the art, there are procedures in which no processing fluid is added to or pumped via segment 41 into filter 20. Rather, only filtrate may be pumped out of filter 20 through segment 42 in these procedures.

Though not shown in FIGS. 2 and 3, one or more semi-permeable membranes are disposed in processing unit 20. These membranes keep the blood flow separate from the filtrate or processing fluid flow, although they do provide for transport of certain materials thereacross as is known and understood in the art. In the usual case, waste products are removed from the blood by diffusion and/or convection (and/or filtration) across the membrane. Beneficial substances such as bicarbonate and certain electrolytes may pass from the processing fluid into the blood also by diffusion (and possibly, though to a lesser extent, convection). One of the governing mechanisms for driving materials across the membrane is the pressure difference across the membrane, also known as the trans-membrane pressure (or TMP). Ideally, by controlling the TMP, control can be had of how fast and thus also how many materials pass through the membrane during a given procedure. However, to control the TMP, the pressures on each side of the membrane must be determined. This has been difficult for many reasons. For example, pressure sensors have not been reliably insertable directly into the respective fluid chambers of the filter 20. Also, the fluid pressure drops in value between the inlet to and the outlet from the filter 20. There is thus no single, easily measured, objective pressure value exhibited on either side of the membrane. Therefore, all attempts at determining pressure differentials across a membrane have been and are still approximations.

Further, it is common in using processing apparatuses such as those described above to choose either the processing unit inlet or outlet pressure as representative of the interior pressure on one side of the membrane and subtract from that the corresponding inlet or outlet pressure measured on the other side of the membrane. Thus, either of the pressure values obtained from sensor 28 (P2) or from sensor 29 (P3) could be selected as the representative blood side interior filter pressure. And, the processing fluid pressure from sensor 54 (P4) could be subtracted therefrom to obtain an approximate TMP (note, a processing fluid inlet pressure sensor (not shown) could also alternatively be used as the representative pressure value as well).

Similarly, averages of the pressures on either or both sides have also been used in attempting to better approximate the TMP. Thus, the value obtained from sensor 28 (P2) could be averaged with the value from sensor 29 (P3) by the formula:

$$\frac{P2 + P3}{2}$$

to achieve an approximate blood side pressure value from which the processing fluid side pressure value from sensor 54 (P4) could be subtracted. Hence, an approximate TMP is:

$$TMP = \frac{P2 + P3}{2} - P4.$$

(Similarly here as well, another sensor (not shown) could have been utilized in the inlet side of the processing fluid circuit and then used with P4 to average the processing fluid pressure in the filter 20.) Any or all of these pressure and TMP values could be displayed on display screen 61 for human operator monitoring and/or these values may simply be used by the apparatus 60 in internal monitoring to make internal decisions and/or automatic adjustments to modify the fluid flow parameters.

Note, the above approximations of the TMP have been directed generally toward determining the average TMP along the length of the semi-permeable membrane. Such an average is helpful in determining the overall performance of the semi-permeable membrane. At times, it is also desirable to determine the maximum TMP experienced by the membrane for avoiding damage or failure thereof. However, this maximum TMP is not usually a function of the average experience over the length of the membrane; rather, is felt locally at an area or point where the pressure difference is greatest. This area is usually at the point of the membrane nearest the blood inlet and filtrate outlet. Thus, the maximum TMP is usually monitored by the relation:

TMP=P2–P4.

It is this differential, and the consequent accuracy of which, that is most usually of concern in TPE.

As to the issue of accuracy, another problem with many conventional pressure monitoring systems makes any of these approaches less reliable than may be desired. The accuracy of pressure sensors used in and with many conventional disposable tubing sets is ±10% with a linearity error of ±1%. In general practice, these error margins are acceptable. However, there are procedures in which these margins are less than desirable.

For example, in the therapeutic plasma exchange (TPE) process, the blood plasma and most other blood constituents, except the red blood cells, are removed across the membrane. Large pressure differentials are established across the membrane to force these materials through the membrane. However, these pressure differentials must be closely controlled to protect the red blood cells remaining on the blood side of the membrane. If the pressure differential is too large, the red blood cells may become damaged or hemolyzed by high pressure contact and/or by high pressure shear forces causing the red blood cells to be partially forced into the pores of the membrane, thereby creating a danger to the patient.

The present invention is intended, in the preferred embodiment, to compensate for these inherent ±10% errors (with or without the linearity errors) of such pressure sensors to arrive at better, safer approximations of TMP's for use in TPE.

To better describe the present invention, some conventional pressure sensing technologies will first be addressed. The pressure sensors 27, 28, 29 and 54 used herein are preferably of a diaphragm type. However, other forms may be substituted as well. Either way, the pressure sensors used in this field are often separated into two distinct parts. This is because the tubing segments 14, 16 and 42, and all other flow components which come into contact with blood and/or blood waste products are preferably disposable. The pressure sensors or at least the blood side components of these sensors are thus also preferably disposable. The electrical transducers are generally expensive and are thus preferably incorporated into apparatus 60 and are then reusable.

Figure 4:
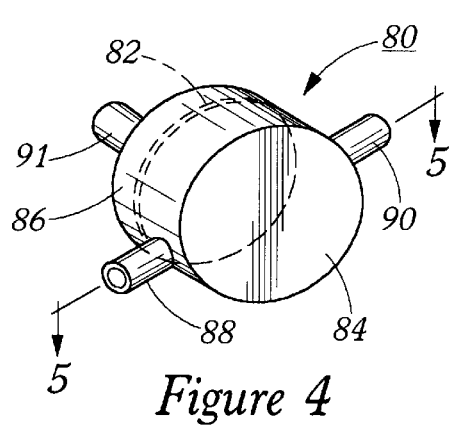
FIG. 4 is an isometric view of a disposable pressure component which may be used in accordance with the present invention.

As is known in the art, a preferred sensor system, with disposable components, will now be described with reference to FIGS. 4, 5, and 6. The disposable portions of the pressure sensors are shown generally in FIGS. 4 and 5, and described as follows. Each disposable portion of a pressure sensor includes a rigid, preferably plastic casing (hereafter called a "pod") 80. The pod has a diaphragm 82 disposed therein. The diaphragm 82 separates the rigid plastic casing into two fluid-tight compartments 84 and 86. An inlet 88 and an outlet 90 open into one of these compartments 84 to allow fluid to flow into and through that compartment (hereafter, designated the flow side compartment) 84. The other compartment 86 on the opposing side of the diaphragm preferably has only one access 91 for fluid communication preferably with a dry gas such as air (although wet/wet transducers are also usable herewith). This compartment is hereafter referred to as the transducer side compartment 86 because a transducer is in pressure-sensing communication with the fluid (here, a dry gas) on this side of diaphragm 82. This pressure pod 80 with diaphragm 82 is the disposable part of the pressure sensor. As used with a preferable processing apparatus 60, apparatus 60 has a corresponding receptacle in and/or to which each disposable pod is connected (see FIG. 6 and the description thereof appearing below); the transducer side access 91 being put in fluid communication with a discrete pressure sensing transducer disposed in the processing apparatus 60. The transducer side access 91 is also simultaneously put in fluid communication with an internal control unit fluid tubing system 100 to be described further below.

Figure 5:
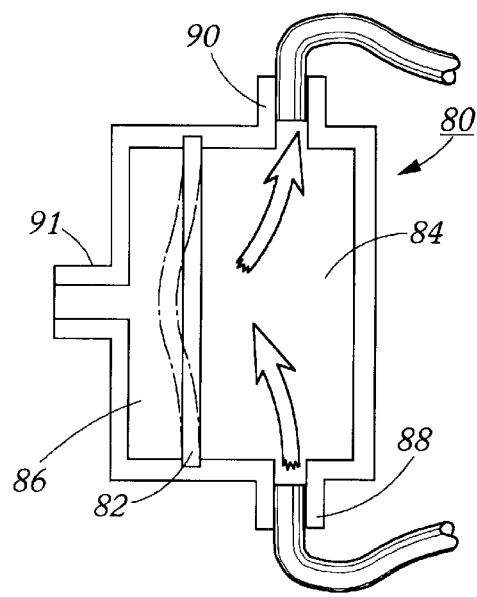
FIG. 5 is a cross-sectional view of the disposable pressure component of FIG. 4 taken along line 5—5 thereof.

As shown in FIG. 5, fluid flowing through the flow side compartment 84 of such a pressure pod 80 has an inherent fluid pressure which acts on the diaphragm 82 by moving it. When the diaphragm moves, the diaphragm either compresses or allows expansion of the fluid/dry gas on the transducer side of the diaphragm. Compression of the fluid in compartment 86 is generally shown using dashed lines in FIG. 5. The pressure of the compressed or expanded fluid is sensed by the corresponding pressure transducer inside the control apparatus 60. Such transducers are schematically shown in FIG. 6. The pressure transducer converts the sensed pressure to an electrical signal which is sent to an electrical microprocessing unit (not shown) which interprets the signal as a pressure value and can then process the signal for display, storage or use by software (or hardware) for calculations, inter alia. These options will be addressed further below.

Note, other pressure pod styles may also be used. For example, pods having only a single access port on the flow side of the diaphragm are known and can be used here. Also, sealed transducer side integral sensing units could also be adapted for use here. However, use of a reference transducer (such as the return sensor, see below) would be preferred over such an adaptation, as the internal pressure system 100 would be less simply usable for generating reference pressures for such sealed units.

Figure 6:
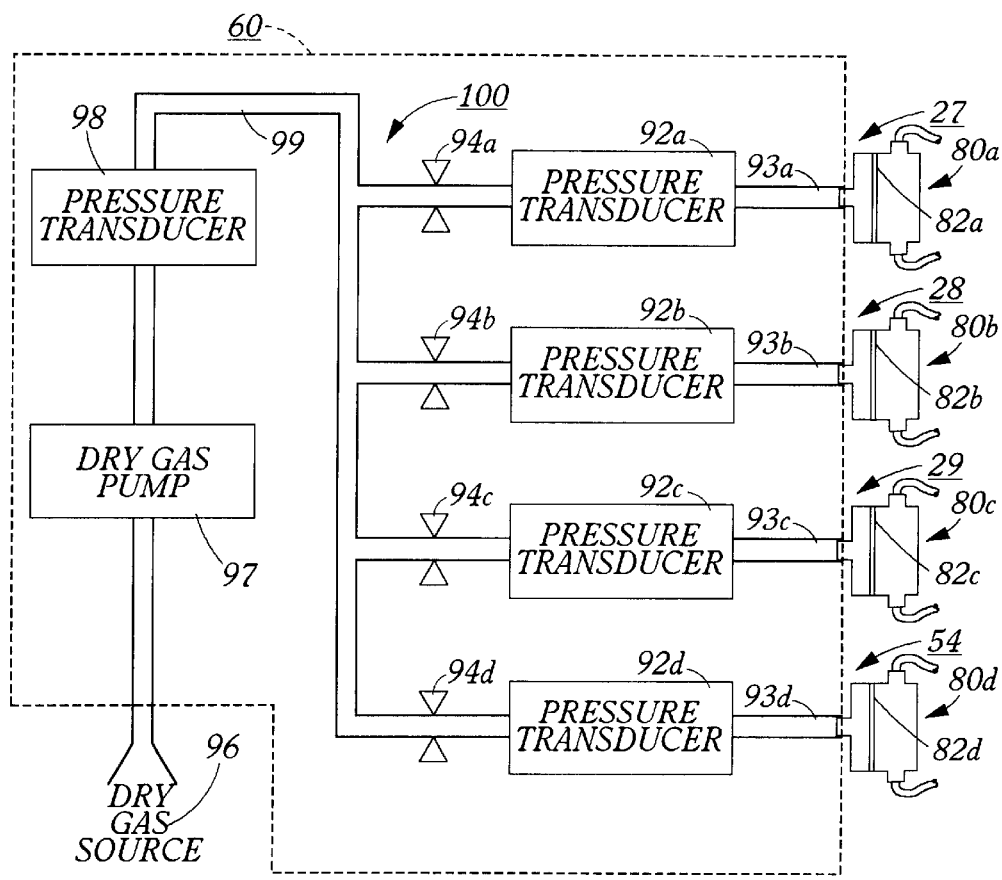
FIG. 6 is a schematic diagram of a pressure tubing system which may be internally incorporated into the apparatus shown in FIGS. 2 and 3.

As shown schematically in FIG. 6, pressure transducer(s) 92(a–d) disposed inside the apparatus 60 (which is depicted here by dashed lines) sense the pressure(s) of the fluid(s) in the internal tubing line(s) 93(a–d). In operation, the valve(s) 94(a–d) behind the transducer(s) 92(a–d) are closed and thus discrete compressions or expansions of the respective fluid in each internal line 93(a–d) caused by fluid flowing in the corresponding exterior pod 80(a–d) is sensed by the respective transducer 92(a–d). The components to the left of the valves 94(a–d) serve functions generally distinct from the pressure sensing operation just described. Here, the left side components comprise a dry gas source 96, a dry gas pump 97 and a system pressure transducer 98 all connected by an internal tubing line 99. These components, together with the transducers 92(a–d), the transducer valves 94(a–d) and the transducer lines 93(a–d), comprise the internal pressure system 100 of apparatus 60. The pump 97 is used, other than in the present invention, primarily to pressurize the transducer sides of the pod diaphragms 82(a–d) to their neutral position(s). It does this by periodically individually pressurizing a respective transducer line 93(a–d), one at a time, to push (or pull) the diaphragm back to its neutral position to increase the future accuracy of its pressure sensing function. Pressure system 100 may also used for creating correction pressure values in the present invention as will be described below.

As mentioned, conventional machines in this art have previously calculated trans-membrane pressures using, for example, averaged pressure values. Other machines have used stored parameter values for comparison with later measured parameter values, such as for determining whether an access or return pressure has changed too much thereby indicating a disconnection.

However, in the present invention, features such as these (calculation and data storage) will be implemented together in a distinctive fashion. For example, after priming but preliminary to use on a patient, all the pressure pods 80(*a–d*) in the preferred embodiment are pressurized on the transducer side to various pre-selected pressures by the internal dry gas pump 97. The corresponding measured pressure values are then stored in a storage data table by the system software (or hardware or firmware). These measured pressure values are then used by the system software (or hardware, or firmware) during patient operation as correction values for calculating better approximations of the actual trans-membrane pressure (TMP) experienced across the semi-permeable membrane.

Figure 7:
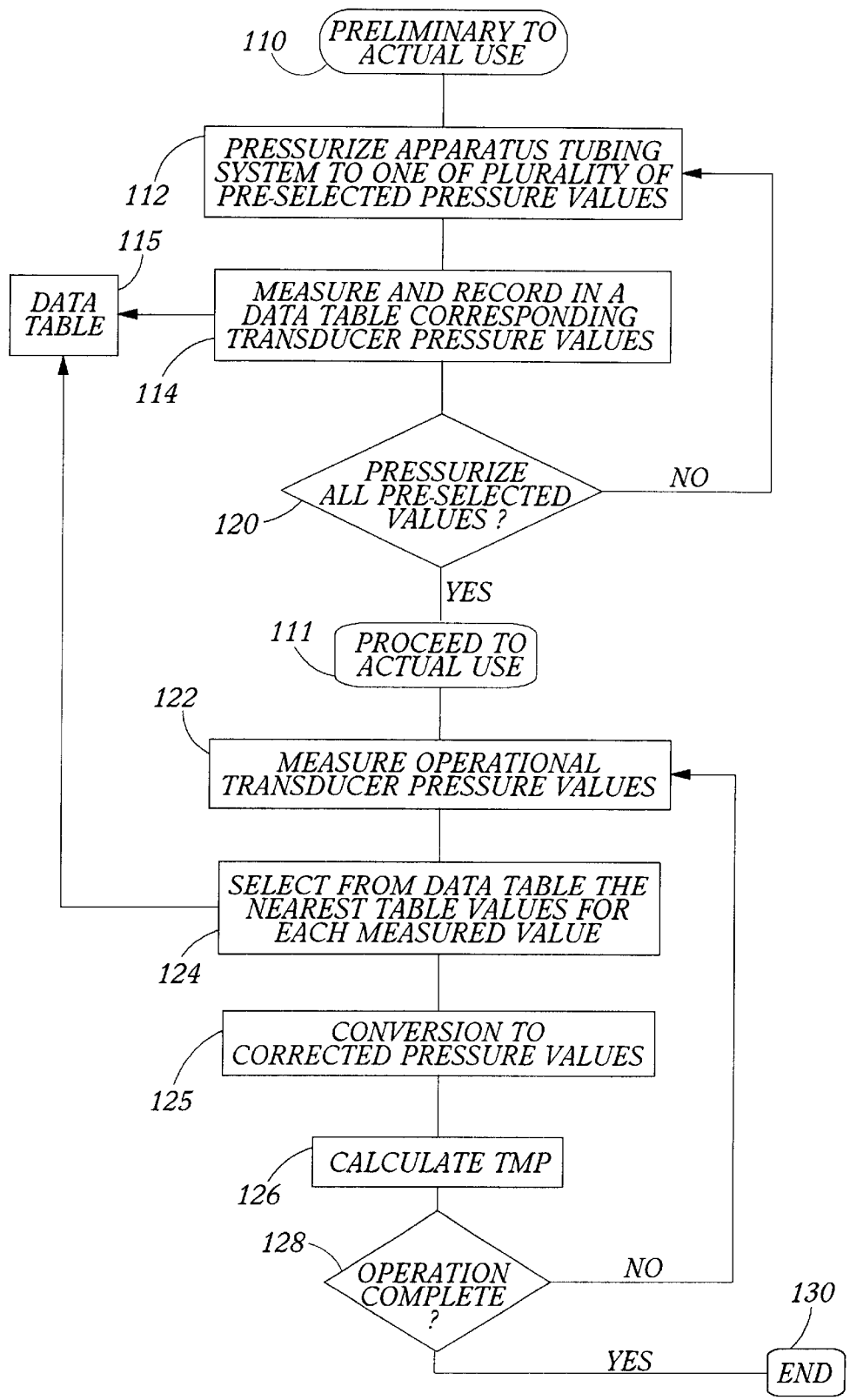
FIG. 7 is a block diagram showing a method for improved parameter monitoring according to the present invention.
Figure 8:
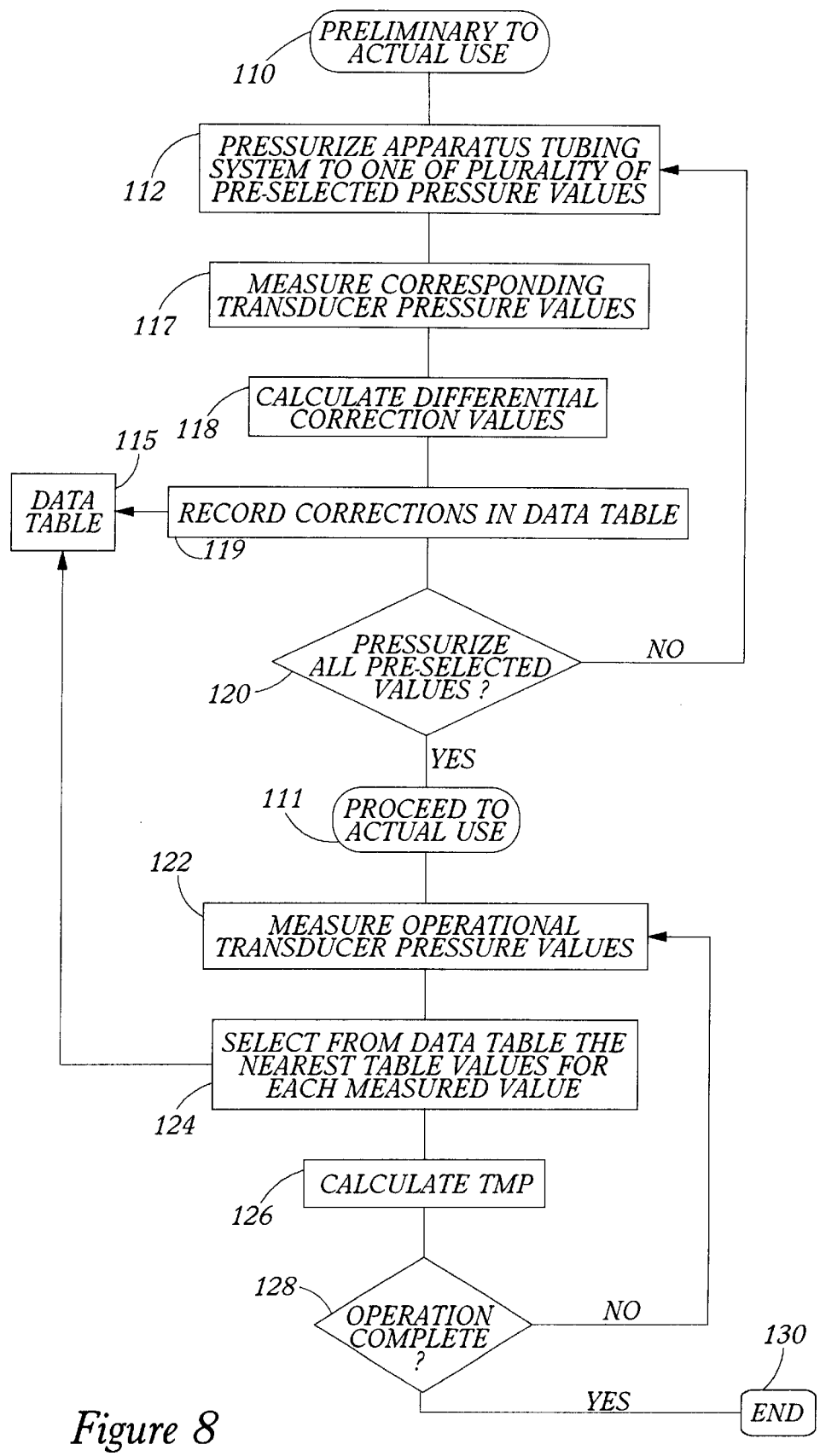
FIG. 8 is a block diagram of an alternative method for improved parameter monitoring according to the present invention.

In particular, and as can be seen from FIGS. 7 and 8, the steps to be taken to calculate the TMP according to the present invention are generally as follows. First, there are two general phases of operation; the preliminary phase prior to actual use, and the actual use phase on a patient. The initial points of these phases are identified in FIGS. 7 and 8 by the reference numbers 110 and 111 for the preliminary and actual use phases, respectively. In the preliminary phase 110 after the tubing lines and processing unit 20 have been loaded on the apparatus 60 and primed with priming solution (according to procedures known in the art), then the preliminary phase 110 is initiated and internal tubing system 100 is pressurized to one of a preferable plurality of pre-selected pressure values. This pressurization step is represented by block 112 in FIGS. 7 and 8. Then, as shown in FIG. 7 by block 114, the corresponding transducer pressure values are measured and recorded in a data table 115. In FIG. 8, an intermediate step of calculating one or more differential correction values is inserted between the steps of measuring and recording. These three steps; measuring, calculating and recording are represented by blocks 117, 118 and 119, respectively in FIG. 8. Note, the respective data tables, both labeled with the identification numeral 115 in FIGS. 7 and 8, may be identical to or distinct from each other depending on the hardware, software or firmware used.

A first decision box 120 in both FIGS. 7 and 8 signifies a process loop for returning to the pressurization step 112 for pressurization of the internal system 100 to another pre-selected pressure value applied to all of the pressure transducers 92(*a–d*). Note also that external pressurization means may also be used as an alternative to or in the absence of an internal system 100. Thus, a pressure source could be applied to the tubing set at, for example, the patient access and/or return lines or devices, a pressure applied and all transducer values then recorded (FIG. 7) or corrected and recorded (FIG. 8). This alternative would be preferred if sealed pressure sensor units are used. After all of the pre-selected pressure values have been applied and the corresponding measured transducer values (FIG. 7) or corrections (FIG. 8) have been recorded in the data table 115, then the actual use procedure 111 can begin.

The first two steps to be taken during actual use as shown in both FIGS. 7 and 8 are to measure the respective pressures exhibited by the fluids flowing through the pressure pods 80(*a–d*), as represented by box 122, and then to consult the data table and select the nearest recorded value or values per box 124 for use in the ultimate TMP calculation step 126. However, the procedure shown in FIG. 7 includes an intermediate step 125 of conversion prior to the TMP calculation 126. Conversion may simply involve a form of interpolation or other correction quantity manipulation as described below. Moreover, though shown as a separate step in FIG. 7, the TMP formula used in step 126 may be modified to incorporate entirely the conversion or interpolation equation (s) of step 125, thereby rendering step 125 superfluous as a discrete step and thus not separately necessary. It has been kept separate to this point to facilitate the description. After the calculation step 126, the apparatus 60 may then decide (based upon pre-programmed or user programmable instructions) whether to automatically adjust pump speeds on one or both sides of the membrane in order to adjust the TMP experienced in filter 20. Thus, the calculated TMP step can include this resulting pump adjustment step. An alarm condition may alternatively be programmed or programmable as a result. Or, the TMP results may simply be displayed for a user to evaluate continuously or periodically Either way, a second decision box 128 is then provided for determining when the actual use procedure has reached completion. If not complete, then the actual use procedure is re-initiated beginning with the measurement step 122. Or, if the procedure has reached completion, the end phase is represented by the end box 130.

The preferred means for accomplishing these steps will now be addressed in detail. However, some variable naming conventions will first be defined to ease the description.

First, the four fluid flow pressure sensors 27, 28, 29 and 54 which have been fairly generically referred to above, will now hereafter be referred to by descriptive names such as sensor 27 hereafter being referred to as the access sensor 27, sensor 28 being the filter sensor 28, sensor 29 being the return sensor 29, and sensor 54 being the waste sensor 54. These names are derived logically from the location of each sensor relative to its nearest non-pump functional unit; access sensor 27 is adjacent the patient access device 17, filter sensor 28 is adjacent the inlet to the filtration unit or filter 20, return sensor 29 is near the patient return device 19 and the waste sensor is in the waste line 42 draining to waste receptacle or bag 53.

The pressure values measured at each of these sensors may then be reduced to variables such as F for the pressure values associated with filter sensor 28, R for the values of return sensor 29 and W for the values of waste pressure sensor 54, for example. Subscripts will also be used to further define which values are being used. For example, $F_a$ represents the actual or applied pressure at the filter sensor 28 whereas, $F_m$ represents the pressure value measured by filter sensor 28 (noting that due to the transducer error margins, $F_m$ should but likely will not equal $F_a$). Similar a and m subscripts are used for the R and W variables, as well as for the trans-membrane pressure variable, TMP.

Further subscripting is also used hereinbelow for the values stored in the data table as well as for those measured during operation. For example, in some versions of the present invention, both the actual pre-selected value applied to a sensor and the corresponding preliminarily measured value will be stored in the data table. However, since a plurality of each of these corresponding values will preferably be stored in the data table, corresponding sequential numbers can be used to keep track of all the corresponding values in a given value set corresponding to a single preliminarily applied pressure value. For example, a subscript numeral 1 is added for the first set of preliminarily measured and then stored values corresponding to the first preliminarily applied pressure value. Thus, $F_{a1}$ (the applied value) corresponds with $F_{m1}$ as well as with $W_{a1}$, $W_{m1}$ and $R_{a1}$ and $R_{m1}$; while $F_{a2}$ corresponds with $F_{m2}$ as well as with $W_{a2}$, $W_{m2}$, $R_{a2}$ and $R_{m2}$, for the second set of preliminarily established values (note, $F_{a1}=W_{a1}=R_{a1}$ and $F_{a2}=W_{a2}=R_{a2}$). Subscripts 3 and 4, inter alia, will also be used for further table values as will become clear. These values can then be used to determine or approximate unknown, operationally measured x or y values such as the actual $F_{ax}$ which corresponds to a measured $F_{mx}$ and a $W_{ax}$, $W_{mx}$, $R_{ax}$ and $R_{mx}$ as well. The variables x and y are generally intended to represent any set of corresponding operational values outside or between sets 1 and 2, or 3 and 4, for example. Thus, a similar value set may be determined for a second operational value set, y, as in $F_{ay}$, $F_{my}$, $W_{ay}$, $W_{my}$, $R_{ay}$, $R_{my}$. Or, still further variable sets may also be used as desired.

Generally during the operation phase, at any given point in time, an $F_{mx}$ will be measured from which all other x values will be determined or approximated by reference to the data table and calculation as necessary. At or near that point in time, a distinct $W_{my}$ value will be measured with its corresponding y values derived or approximated from the data table and calculation as necessary. It is through use of these associated x and y values that a correction or modification to $F_{mx}$ and/or $W_{my}$ can be achieved to develop a corrected or modified TMP. Thus, in general $TMP_{corrected}=F_{mx_{corrected}} - W_{my_{corrected}}$, which is also represented as $TMP_c = F_{mx_c} - W_{my_c}$. Usually, the corresponding actual ax and ay values are the ultimately sought values for obtaining $TMP_c$. However, since the transducer errors are not completely eliminated hereby, the ax and ay values are not necessarily obtained. Although, if the errors could eliminated, then, the ax and ay values would be the corrected or modified values such that $F_{mx_c} = F_{ax}$ and $W_{my_c} = W_{ay}$ so that $TMP_c = F_{ax} - W_{ay}$.

A first example according to the present invention will now be described.

In one instance of building a pre-operational value data table as in performance of the first two steps according to the flow chart shown in FIG. 7, the following list of typical measured values were obtained. Note, the applied values represented below are those applied by an internal tubing system 100 and pump 97 as established by internal system transducer 98. If a zero error could be assumed for the measurements of the internal system transducer 98, then these applied values would also represent actual pressure values with the filter and waste measurements showing their inherent measurement errors.

TABLE 1

Pre-Operation Applied Values and Corresponding Sensor Readings

| Applied Pressure Values ($F_a$ and $W_a$) mmHg | Filter Sensor Reading ($F_m$) mmHg | Waste Sensor Reading (Wm) mmHg |
|---|---|---|
| −50 | −63 | −63 |
| 0 | −4 | −4 |
| 50 | 47 | 44 |
| 100 | 101 | 96 |
| 150 | 152 | 146 |
| 200 | 203 | 196 |
| 250 | 257 | 247 |
| 300 | 309 | 298 |
| 350 | 359 | 345 |
| 400 | 412 | 397 |
| 450 | 463 | 445 |
| 492 | 534 | 486 |

Figure 9:
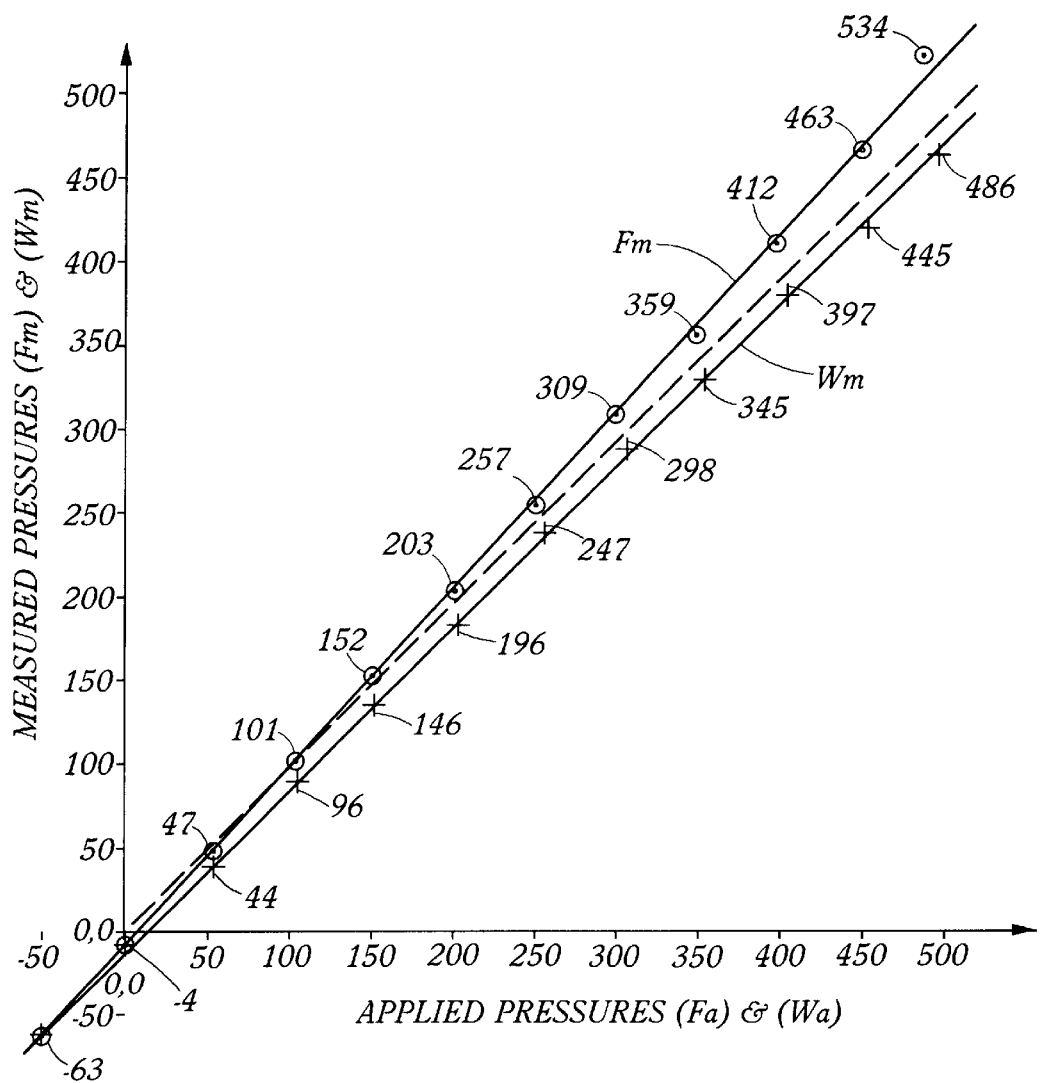
FIG. 9 is a graphical representation of an example of preliminarily applied pressure values and the corresponding preliminarily measured pressure values.

These values ($F_a$, $W_a$, $F_m$ and $W_m$) are shown graphically in FIG. 9 with the applied values presented horizontally along the X-axis and the corresponding measured values ($F_m$ and $W_m$) along the Y-axis. A solid line has been drawn for each of the sets of measured values ($F_m$ and $W_m$) and a dashed line has been drawn representing an ideal zero error condition where the actual or measured value would equal the applied value. Note, a single data table can be created and used as shown here in Table 1, or separate tables for the F and W values may be maintained. This is true also for the R (or even the access, A) values (not shown in Table 1) if used; they may all three (or more) be stored in one table or in separate tables.

Using FIG. 9 it will now be shown that a form of curve fitting will provide better accuracy in pressure monitoring and is thus a preferred method for use in pressure sensitive procedures such as TPE. More particularly, operationally measured pressures will be shown to be modified to better reflect the actual pressures occurring in the respective fluid containers (including e.g., the respective filter chambers, compartments, or like fluid flow channels or in the tubing lines or the respective pods or casings or even in the bags, inter alia) at or near the respective pressure sensors 27, 28 and 54. This curve fitting is one form of conversion per block 125 of FIG. 7, and again, this conversion can be performed simultaneously with the end calculation of block 126.

In particular, a simplified form of curve fitting according to the present invention involves either single or double point interpolation using the nearest recorded values as the interpolation reference. Remembering the variable naming conventions set forth above, the sought-after operational, unknown filter value is $F_{ax}$. $F_{ax}$ is the approximate, near actual pressure value which corresponds to the operationally measured filter value $F_{mx}$. $F_{ax}$ better represents the actual pressure being exhibited adjacent the filter sensor 28 and $F_{ax}$ is therefore the value sought here for use in the ultimate TMP calculation. According to the flow chart of FIG. 7 and assuming FIG. 9 represents the data stored in data table 115 pursuant to steps 112 and 114, once a filter value, $F_{mx}$, is measured in operation, the next step is to consult the data table 115 and select the nearest data values stored therein. Then, these values can be used to find a corresponding $F_{ax}$ through interpolation, curve-fitting or ratioing. A single point ratioing can be used as in $$\frac{F_{ax}}{F_{mx}} = \frac{F_{a1}}{F_{m1}}$$

whereby $F_{a1}$ and $F_{m1}$ represent the closest recorded data point found stored in the table 115 relative to $F_{mx}$. Then, $$F_{ax} = F_{mx} \cdot \frac{(F_{a1})}{(F_{m1})}$$

Using as an arbitrary example an operationally measured $F_{mx}$ of 275 mmHg, the data table 115, as represented by Table 1 and FIG. 9, reveals that the nearest single recorded data point ($F_{a1}$, $F_{m1}$) is that point where $F_{m1}$ is 257 mmHg, with a corresponding $F_{a1}$ of 250 mmHg. In other words, $F_{m1}$=257 is the closest recorded m value in the data table to the operationally measured $F_{mx}$ of 275 mmHg. Thus, continuing the example, $$F_{ax} = F_{mx} \cdot \frac{(F_{a1})}{(F_{m1})} = 275 \cdot \frac{(250)}{(257)} = 267.5 \text{ mmHg}$$

Depending upon the linearity of the data table values, another, potentially better approximation may be derived from a two point linear interpolation as in the formula:

$$\frac{F_{ax}}{F_{mx}} = \frac{F_{a2} - F_{a1}}{F_{m2} - F_{m1}}$$

whereby $F_{a2}$ and $F_{m2}$ represent a second close, recorded data point relative to $F_{mx}$. Preferably though not necessarily, this second data point ($F_{a2}$, $F_{m2}$) is the next higher data point from $F_{mx}$ and the first data point ($F_{a1}$, $F_{m1}$) is the next lower data point. Again, using the arbitrary example of an operationally measured value of $F_{mx}$=275 mmHg, the second data point is found from Table 1 and/or FIG. 9 to be $F_{m2}$=309 mmHg with a corresponding $F_{a2}$=300 mmHg. Thus the above two point equation becomes:

$$F_{ax} = F_{mx} \cdot \frac{(F_{a2} - F_{a1})}{(F_{m2} - F_{m1})} = 275 \cdot \frac{(300 - 250)}{(309 - 257)} = 264.4 \text{ mmHg}$$

Or, by a further refinement in two point interpolation where, $$\frac{F_{ax} - F_{a1}}{F_{mx} - F_{m1}} = \frac{F_{a2} - F_{a1}}{F_{m2} - F_{m1}};$$

such that $$F_{ax} = \frac{F_{a2} - F_{a1}}{F_{m2} - F_{m1}} \cdot (F_{mx} - F_{m1}) + F_{a1};$$

which according to the above example, simplifies to $$F_{ax} = \frac{300 - 250}{309 - 257} \cdot (275 - 257) + 250 = 267.3 \text{ mmHg}$$

Numerous similar interpolation, curve-fitting and ratio relationship possibilities exist and are intended within the scope of the present invention.

A corrected waste value $W_{ay}$ could also be found in any of these ways by selecting from the data table 115 (for example; Table 1 and/or FIG. 9) the closest $W_{a3}$, $W_{m3}$ values with or without $W_{a4}$, $W_{m4}$ values. The use of subscripts 3 and 4 is intended to show that different table values are preferably consulted for the W values as opposed to the F values. The operationally measured $W_{my}$ may and likely will have different data table points closer thereto. Thus, $W_{m3}$, $W_{a3}$ represents a first data table point close to $W_{my}$, and $W_{m4}$, $W_{a4}$ represents a second close data table point. Then a corrected $TMP_c$ could be calculated (per step 126, in FIG. 7) using the general formula:

$$TMP_c = F_{ax} - W_{ay}.$$

Further, as mentioned above, the separate step of conversion or interpolation could be eliminated by incorporating the interpolation table values directly into the ultimate TMP calculation. For example, using the single point method $TMP_c$ becomes:

$$TMP_c = F_{ax} - W_{ay} = F_{mx} \frac{(F_{a1})}{(F_{m1})} - W_{my} \frac{(W_{a3})}{(W_{m3})};$$

where $F_{mx}$ and $W_{my}$ are the operationally measured values of F and W taken from respective sensors 28 and 54. Operationally measured means taken during the operation phase.

Note also that $F_a = F_{a1}$ does not equal $W_a = W_{a3}$. Rather $F_{a1}$ is found from the data table 115 as the value corresponding to the $F_{m1}$ table value which is nearest to the operationally measured $F_{mx}$. $W_{a3}$ is found in the same fashion from its distinct table set of W values as the corresponding value to the $W_{m3}$ table value which is nearest the operationally measured $W_{my}$.

Similarly, the use of the first two point interpolation derived above would generate a $TMP_c$ formula of:

$$TMP_c = F_{ax} - W_{ay} = F_{mx} \cdot \frac{(F_{a2} - F_{a1})}{(F_{m2} - F_{m1})} - W_{my} \cdot \frac{(W_{a4} - W_{a3})}{(W_{m4} - W_{m3})};$$

with the same notes about subscripts 1, 2, 3 and 4 as set forth above. Again, numerous interpolation formulas can be substituted herein; including the second two point interpolation formula derived above, such that $$TMP_c = \frac{F_{a2} - F_{a1}}{F_{m2} - F_{m1}} \cdot (F_{mx} - F_{m1}) + F_{a1} - \frac{W_{a4} - W_{a3}}{W_{m4} - W_{m3}} \cdot (W_{my} - W_{m3}) - W_{a3}.$$

As a second general method, the return pressure sensor 29 and values measured thereby may also be used in modifying the filter and waste pressure values to improve TMP accuracy. Generally, this entails using the return pressure sensor to represent the applied value from the above examples. Thus, the internal transducer 98, and values measured thereby during preliminary pressurization is not necessarily used in this example at least not in the calculations or data storage. A more detailed step through process using the return values as the references will now be described.

First, when priming is complete, the filter, return, and waste pressures are noted and these values shall be referred to as the initial priming pressure values. These may be recorded in the data table. The internal tubing system line 99 (see FIG. 6) is set to a neutral initial pressurization value such as 0 mmHg and then the filter, return and waste valves 94 b, c and d (FIG. 6) are opened simultaneously and allowed to stabilize. These initial steps are preferred but may not be necessary depending on the equipment (sensors, etc.) being used.

Then, using the value measured by the return transducer 92c as the reference standard, the internal line 99 is pressurized with the dry gas pump 97 to the point where transducer 92c measures a first preselected pressurization value such as −50 mmHg, for example. The filter, waste, and return pressures are preferably then allowed to stabilize. Next, the corresponding measured filter, waste, and return pressure values are recorded in the data table 115 where the return pressure value remains equal to this first pressurization value (e.g., −50 mmHg.). These recorded pressure values are hereafter referred to as correction pressure quantities, $F_{m1}$, $W_{m1}$ and $R_{m1}$ (or other numerical subset variables, such as 2, 3 or 4, e.g.), as described above: Note, even though $R_m$ is a measured value, it also represents the applied value in correspondence to the applied values addressed in the first example above (thus, in this example, $R_{m1} = R_{a1} = F_{a1} = W_{a1}$).

The above two steps of pressurization and recording are repeated for various preliminarily applied pressures such as for 0, +50, +100, +150, +200, +250, +300 +350, +400, +450, +500 mmHg, for example. Numerous alternative preselected applied pressure values may also be used. The data table 115 is then completed.

Then, all of the internal line valves 94a–d (FIG. 6) are closed and the filter, waste, and return pressure values are restored to their initial priming values noted above.

The apparatus is then ready for patient operation, and during the patient run, the TMP is calculated as follows:

First, an operational filter value $F_{mx}$ is measured on filter sensor 28;

Then, in the data table 115, the filter correction pressure values (here, $F_{m1}$, $R_{m1}$) (which is analogous to the data point ($F_{m1}$, $F_{a1}$) used in the above examples) closest to the measured filter value $F_{mx}$ are selected.

Linear interpolation is then used to convert the measured filter pressure $F_{mx}$ into a corrected filter pressure, $F_{ax}$, as above. A preferred interpolation formula for this second method is derived as follows (noting that the simpler interpolation formulas introduced above could be used here as well):

$F_{m1}$ is defined as the lower recorded filter correction pressure value (this is the same as $F_{m1}$, above); and $F_{m2}$ is defined as the upper recorded filter correction pressure value ($F_{m2}$, above).

Similarly, $R_{m1}$ is defined as the recorded return pressure that corresponds to the lower filter correction pressure, $F_{m1}$. Thus, $R_{m1}$ is the same value conceptually as $F_{a1}$, above, the difference being that $R_{m1}$ here was measured by the return sensor 29 as opposed to the internal system transducer 98 (which gave the applied pressure value); and $R_{m2}$ is defined as the return pressure that corresponds to the upper filter correction pressure, $F_{m2}$ (Again, $R_{m2}$ is like $F_{a2}$ except as noted for the $R_{m1}$ and $F_{a1}$ relation above).

Then, by linear interpolation in the same fashion as the last interpolation formula set forth above;

$$F_{ax} = \frac{R_{m2} - R_{m1}}{F_{m2} - F_{m1}} \cdot (F_{mx} - F_{m1}) + R_{m1}.$$

(Note, $R_{m2}$ and $R_{m1}$ appear as if substituted for $F_{a2}$ and $F_{a1}$, respectively, from the last formula.)

The corrected waste pressure is interpolated also according to the last interpolation formula such that;

$$W_{ay} = \frac{R_{m4} - R_{m3}}{W_{m4} - W_{m3}} \cdot (W_{my} - W_{m3}) + R_{m3}.$$

(As above, $R_{m4}$ and $R_{m3}$ are merely substituted for $W_{a4}$ and $W_{a3}$, respectively, in the most recently developed interpolation formula above. The subscripts 3 and 4 are intended merely to signify that distinct table values will likely be found relative to the operationally measured $W_{my}$.)

The corrected TMP is then calculated per the following equation:

$$TMP_c = F_{ax} - W_{ay}.$$

And, as above, the interpolation equations could be substituted into the final TMP equation such that $$TMP_c = F_{ax} - W_{ay}$$
$$= \frac{R_{m2} - R_{m1}}{F_{m2} - F_{m1}} \cdot (F_{mx} - F_{m1}) +$$
$$R_{m1} - \frac{R_{m4} - R_{m3}}{W_{m4} - W_{m3}} \cdot (W_{my} - W_{m3}) + R_3.$$

Note, the access transducer 92a (corresponding to access sensor 27) could also be used as the initial reference standard in an embodiment such as this.

Also with this embodiment, using the return (or access) transducer as the reference standard for the corrections, the concept of using an external pre-pressurization system may be easily understood. Thus, instead of building a data table 115 using the internal pressure system 100 to apply the various pre-selected pressures to the filter, waste and return (or access) transducers; an external pressurization device (not shown) could be applied to the tubing system (both the blood and processing fluid circuits 12 and 40), before or preferably after priming. Then, this external pressurization system could be used to sequentially supply the pre-selected pressurization values, using the return (or access) transducer as the reference, and the corresponding filter and waste pressures can then be stored in the data table as before. Indeed, all other steps would proceed as before. An internal pressurization system 100 may still be disposed in the apparatus 60 for other uses (diaphragm repositioning), or it could be eliminated. From this, it can be understood that back side sealed pressure sensors (vacuum sealed or the like) could be used herewith, all other steps still proceeding as described. Principally, this means any sensor can be used herewith so long as it can be pre-pressurized (front or back) to various pre-selected pressure values and the corresponding preliminarily measured values then stored in a data table for later use in modifying the operationally measured pressure values. Note, if no internal system 100 or the like, is used, then the external pressure source will need to be connected to pressurize both the primary and secondary circuits 12 and 40 simultaneously so that the barrier therebetween, the semi-permeable membrane in the primary example, will not be damaged.

Note, display screen 61 may provide a display of the functioning of the TMP measurement. This screen may display the filter pressure, the waste pressure, and selected correction values, including the corrected TMP=$TMP_c$.

Help display screens can be provided to explain why the $TMP_c$ is different from the mere subtraction of the waste pressure value from the filter pressure value. The help screen can note that the $TMP_c$ is the corrected Filter Pressure minus the corrected Waste Pressure corrected for the accuracy errors inherent in the sensors on the machine.

The display 61 need not show all or any of these values as the apparatus 60 may also be programmed to interpret the operational TMP values and automatically adjust various flow parameters (such as pump speed) to bring the TMP to a preferred preselected value. Thus, no specific measurements need be shown with such internal monitoring.

A third approach will now be described. First, consider a TMP correction scheme similar to those described above. This third scheme also involves pressurizing the filter and waste transducers to a set of fixed pressures such as those used above (−50 mmHg, 0, +50 mmHg, . . . , +450 mmHg and/or +500 mmHg). However, here, as shown in FIG. 8, at each preliminary pressurization value, the difference between the corresponding preliminarily measured filter and waste pressures is recorded in the data table 115 as a correction quantity. The correction quantity is used later to modify the operationally measured TMP, so that the corrected TMP (=$TMP_c$) is closer to the actual pressure difference experienced by the membrane.

The correction quantities for this third method are defined as follows.

The formula defining the correction quantity to be recorded in table 115 is as follows. First, $C_s$ is defined as the correction quantity at a particular preliminarily applied system pressure $F_{as}=W_{as}$ as stored in the data table 115. Then, by the above description of this third approach, the correction quantity is the difference between the filter and waste values at S; $C_s = F_{ms} - W_{ms}$. $C_s$ is thus the stored correction quantity when the applied pressures $F_{as} = W_{as}$. S as a subscript variable generally corresponds to the recorded value sets 1, 2, 3 and 4 used and described relative to the first and second approaches above.

The corrected TMP=$TMP_c$ is defined for this third approach at an operationally measured $F_{mx}$ and $W_{my}$ as;

$$TMP_c = F_{mx} - W_{my} - \tfrac{1}{2}C_{sx} - \tfrac{1}{2}C_{sy}.$$

In this formula, $C_{sx}$ is defined as the correction quantity $C_s$ which corresponds to the stored $F_{ms}$ which is nearest to the operationally measured value $F_{mx}$. This could also be written in terms of the corrected or modified $F_{ax}$ relative to the measured $F_{mx}$ as $F_{ax} = F_{mx} - \tfrac{1}{2}C_{sx}$. Similarly, $C_{sy}$ is the correction quantity corresponding to the stored $W_{ms}$ which is nearest to the operationally measured $W_{my}$. Therefore, $W_{my}$ could be corrected to achieve a $W_{ay}$ as $W_{ay} = W_{my} + \tfrac{1}{2}C_{sy}$. This is how the correction quantities are defined as the closest stored correction quantities in the data table to the respective operationally measured pressures $F_{mx}$ and $W_{my}$. Note, the $C_{sx}$ may be, but likely is not equal to $C_{sy}$ depending only on the nearest $F_{ms}$ and $W_{ms}$ values in the data table 115.

This is different from the first two methods set forth above because here the preference is in storing the calculated corrections, $C = F - W$, in the data table 115, as opposed to merely storing the preliminary values themselves. Also, these are not curve-fitting in the same fashion as the interpolation methods were above. However, it should also be noted that the corrections, $C = F - W$, can also be performed during actual operation immediately prior to, or simultaneously with the ultimate TMP calculation as opposed to being a stored value (the $F_{sx}$ and the $W_{sy}$ values are stored in the data table 115). This sort of procedure can then be generally equivalent to the conversion step represented by block 125 in FIG. 7. And, as before, these conversions can also be rolled into the final calculation step 126. Moreover, these corrections $C = F - W$ could also be viewed as forming a line or curve as in the previous examples, and thus interpolation can be used here also to improve the accuracy of the correction quantities being used.

Next, a fourth approach will be described. This fourth approach is a TMP correction scheme similar to the third approach set forth above; however, this method also uses the return pressure as a standard, and the waste and filter pressures are corrected to correspond to the return for the TMP calculation.

More particularly, this method involves preliminarily pressurizing the filter, waste and return transducers to a similar set of preselected pressure values (such as the −50 mmHg, 0, +50 mmHg, +150 mmHg, . . . , +450 mmHg, +500 mmHg sets used above) but in this method, the difference between the preliminarily measured filter and return pressures are recorded as one correction quantity. A second correction quantity representing the difference between the waste and return pressures is also recorded, and this may be done simultaneously or, the pressurization sequence may be repeated subsequently for the waste and the return transducer relationships. These correction quantities are used to modify the operationally measured TMP so that the calculated $TMP_c$ is closer to the actual TMP exhibited across the semi-permeable membrane.

The corrections for this fourth method are defined as follows.

First, $C_{s1}$ is defined as the correction quantity when the filter transducer is at a first preliminarily applied pressure S1. Then the formula defining the correction is: $C_{s1} = R_{m1} - F_{m1}$ when $F_{a1} = R_{a1}$. $C_{s2}$ is defined as the correction when the waste transducer is at a second pressure S2. Then $C_{s2} = R_{m2} - W_{m2}$ when $W_{a2} = R_{a2}$.

The $TMP_c$ formula for this fourth approach is then defined as:

$$TMP_c = F_{mx} + C_{sx} - (W_{my} + C_{sy}).$$

Note that as in the third method above, the correction quantities to be used are the ones closest to the operationally measured pressure values. Thus, $C_{sx}$ is defined as the correction quantity $C_s$ which corresponds to the stored $F_{ms}$ which is nearest to the operationally measured value $F_{mx}$. This could also be written in terms of the corrected or modified $F_{ax}$ relative to the measured $F_{mx}$ as $F_{ax} = F_{mx} + C_{sx}$. Similarly, $C_{sy}$ is the correction quantity corresponding to the stored $W_{ms}$ which is nearest to the operationally measured $W_{my}$. Therefore, $W_{my}$ could be corrected to achieve a $W_{ay}$ as $W_{ay} = W_{my} + C_{sy}$. This is how the correction quantities are defined as the closest stored correction quantities in the data table to the respective operationally measured pressures $F_{mx}$ and $W_{my}$.

This suggests another way of viewing this correction scheme. In particular, if x=1 and $C_{s1} = R_{m1} - F_{m1}$ and when y=2 and $C_{s2} = R_{m2} - W_{m2}$; then by substituting into the $TMP_c$ definition, this special situation simplifies to:

$$TMP_c = F_{m1} + (R_{m1} - F_{m1}) - [W_{m2} + (R_{m2} - W_{m2})] = R_{m1} - R_{m2}.$$

Note also as above, the $C_{sx}$ may be, but likely is not equal to $C_{sy}$ depending only on the nearest $F_{ms}$ and $W_{ms}$ values in the data table 115.

Moreover, the correction quantities calculated by this method (R−F, and R−W) are preferably stored in the data table during the preliminary phase prior to the actual, operational use phase. However, these manipulations can also be performed during actual operation immediately prior to or simultaneously with the ultimate TMP calculation (steps 125 and 126, respectively). Also, as before, interpolation of these correction values can be performed to improve the accuracy of the resulting correction quantities being used.

Without intending to limit the invention to any particular theory, it is believed that the primary principle of operation for at least this fourth approach is that the difference between two measurements taken by the same transducer (the return transducer R, for example) is more accurate than the corresponding difference between one measurement taken by one transducer and a second measurement taken by a second transducer (the filter F and waste W transducers, respectively, for example). This is because the substantially constant linearity that each of these systems (transducers) exhibits individually is usually better for that single transducer than when the accuracies, even if linear, of two or more transducers are combined. The overall accuracy of two or more transducers is thus less than that for a single transducer.

Brief summaries of operation of these third and fourth methods will now be set forth. The third approach will hereafter also be referred to as the two-transducer method, the fourth approach as the three-transducer method.

In the two-transducer method, the minimum items needed are two transducers whose difference is to be measured in operation; an apparatus to apply identical parametric stimuli to both transducers simultaneously; an apparatus to record the parametric value readings of and/or the differences between the two transducers when they are stimulated identically; and a device or other means for taking operationally measured parametric values and using these to retrieve corresponding recorded parametric values and modifying the operationally measured values with the corresponding recorded values. The general procedure is as follows:

A. Before use, the transducers are stimulated to various values in the range they are likely to measure during use, and the difference in their readings is recorded at each stimulated value.

B. During use, the difference between the transducers is adjusted with a weighted combination of the difference readings recorded in general step A, above. If the weighted combination is chosen properly based on the characteristics of the transducers, the resulting adjusted difference will be more accurate than the unadjusted difference.

In the preferred implementation of measuring the difference between two fluid pressures on opposite sides of a semi-permeable membrane, this general procedure may more specifically be performed as follows:

A. Before use, the two pressure transducers are connected to the stimulus apparatus so that they can be exposed to identical pressures. Then, the transducers are exposed to a series of identical pressures, and the corresponding measurement differences between the two transducers are then recorded.

B. During use, an uncorrected difference measurement would be the measurement of the first transducer minus the measurement of the second transducer (or, Transducer 1–Transducer 2). According to this invention, the corrected difference measurement is the measurement of the first transducer minus the measurement of the second transducer plus a correction (Transducer 1–Transducer 2+Correction). And, the correction is a function of the differences measured and recorded in step A.

In the three-transducer method, the minimum items needed are identical to those for the two-transducer method, above, with the addition of a third transducer. In particular, the items needed are two transducers whose difference is to be measured in operation (hereafter referred to as transducers 1 and 2); a third transducer (hereafter, transducer 3); an apparatus for applying identical stimuli to all three transducers simultaneously; an apparatus for recording the readings of the three transducers when they are identically stimulated; and a device or other means for taking operationally measured parametric values and using these to retrieve corresponding recorded parametric values and modifying the operationally measured values with the corresponding recorded values. The general procedure is as follows:

A. Before use, all three of the transducers are stimulated to various parametric values in the range they are likely to measure in operation, and the actual readings of all three transducers corresponding to each stimulated value are recorded. The differences between the first and third and the second and third transducers are also preferably recorded.

B. During use, the reading of transducer 1 is adjusted to be the reading that transducer 3 provided when all three transducers were identically stimulated at the closest recorded value to the presently operationally measured transducer 1 reading. The same sort of adjustment is performed with transducer 2. Then, instead of the difference reflecting the mere difference of operational readings between transducers 1 and 2 (as in the Difference=Transducer 1–Transducer 2), then the corrected difference is reflected as the difference between two of the stored third transducer reading (or, Difference=Transducer 3 (corresponding to 1)–Transducer 3 (corresponding to 2).

In preferred implementation of measuring the difference between two fluid pressures on opposite sides of a semi-permeable membrane, this general procedure may more specifically be performed as follows:

A. Before use, all three sensors are exposed to identical preliminary pressures. The corresponding values measured by each of the three transducers are then recorded in a related manner. For example, at a first applied pressure the first transducer measures 11, the second measures 9 and the third measures 15. These values are recorded as shown below, and the corresponding measurements of second and third applied pressures are shown as recorded as well:

| Transducer 1 | Transducer 2 | Transducer 3 |
| --- | --- | --- |
| 11 | 9 | 15 |
| 22 | 19 | 25 |
| 33 | 29 | 35 |

B. During use, each operational reading of transducer 1 is adjusted by substituting the corresponding recorded reading that transducer 3 provided during the preliminary phase of step A, above. The same sort of adjustment is performed with transducer 2. Thus, if transducer 1 measured 32, for example, then a value of 35 from the closest corresponding record transducer 3 value will be substituted. And, if transducer 2 measured 10, for example, the table value of 15 would be substituted therefor. Then, instead of the difference being:

Difference=Transducer 1–Transducer 2=32–10=22;

the difference would instead be corrected to:

Difference=Transducer 3–Transducer 3=35–15=20.

Accordingly, a new and unique invention has been shown and described herein which achieves its purposes in an unexpected fashion. Numerous alternative embodiments readily foreseeable by the skilled artisan, which were not explicitly described herein are considered within the scope of the invention which is limited solely by the claims appended hereto.

Accordingly, what is claimed is:

1. A method for determining a parametric difference between first and second fluids in a fluid system, said fluid system having a first and a second fluid container each containing one of the respective first and second fluids, the first fluid container having a first parametric transducer operatively associated therewith, the second fluid container having a second parametric transducer operatively associated therewith, the method comprising the steps of:

a) subjecting the first and second transducers to a pre-selected parametric value;

b) recording in a data table the respective first and second parametric measurements measured by the first and second transducers as a result of being subjected to said pre-selected parametric value, and calling these parametric measurements recorded correction quantities;

c) repeating the above steps a) and b) for a set of pre-selected parametric values;

d) exposing the respective first and second transducers to the respective first and second fluids in the first and second fluid containers in operation; and e) calculating the operational parametric difference as follows:
  1) measuring the first and second operational parametric values;
  2) locating in the data table the recorded correction quantities closest to the first and second operationally measured parametric values;
  3) converting the operationally measured parametric values into first and second corrected parametric values to find the parametric difference according to:

parametric difference=first corrected parametric value−second corrected parametric value.

2. A method according to claim 1 wherein the substep of converting the operationally measured parametric values includes using single point interpolation in which the first corrected parametric value, hereafter called $F_{ax}$, is related to the first operationally measured parametric value, hereafter called $F_{mx}$, relative to the closest recorded correction quantities, hereafter called $F_{a1}$, $F_{m1}$, thereto, by the relation:

$$F_{ax} = F_{mx} \cdot \frac{(F_{a1})}{(F_{m1})};$$

and, the second corrected parametric value, hereafter called $W_{ay}$, is related to the second operationally measured parametric value, hereafter called $W_{my}$, relative to the closest recorded correction quantities, hereafter called $W_{a2}$, $W_{m2}$, thereto, by the relation:

$$W_{ay} = W_{my} \cdot \frac{(W_{a2})}{(W_{m2})}.$$

3. A method according to claim 1 wherein the substep of converting the operationally measured parametric values includes using two point interpolation in which the first corrected parametric value, hereafter called $F_{ax}$, is related to the first operationally measured parametric value, hereafter called $F_{mx}$, relative to the two closest sets of recorded correction quantities, hereafter called $F_{a1}$, $F_{m1}$, and $F_{a2}$, $F_{m2}$, thereto, by the relation:

$$F_{ax} = F_{mx} \cdot \frac{(F_{a2} - F_{a1})}{(F_{m2} - F_{m1})};$$

and, the second corrected parametric value, hereafter called $W_{ay}$, is related to the second operationally measured parametric value, hereafter called $W_{my}$, relative to the two closest sets of recorded correction quantities, hereafter called $W_{a3}$, $W_{m3}$, and $W_{a4}$, $W_{m4}$, thereto, by the relation:

$$W_{ay} = W_{my} \cdot \frac{(W_{a4} - W_{a3})}{(W_{m4} - W_{m3})}.$$

4. A method according to claim 1 wherein the substep of converting the operationally measured parametric values includes using two point interpolation in which the first corrected parametric value, hereafter called $F_{ax}$, is related to the first operationally measured parametric value, hereafter called $F_{mx}$, relative to the two closest sets of recorded correction quantities, hereafter called $F_{a1}$, $F_{m1}$, and $F_{a2}$, $F_{m2}$, thereto, by the relation:

$$F_{ax} = \frac{(F_{a2} - F_{a1})}{(F_{m2} - F_{m1})} \cdot (F_{mx} - F_{m1}) + F_{a1};$$

and, the second corrected parametric value, hereafter called $W_{ay}$, is related to the second operationally measured parametric value, hereafter called $W_{my}$, relative to the two closest sets of recorded correction quantities, hereafter called $W_{a3}$, $W_{m3}$, and $W_{a4}$, $W_{m4}$, thereto, by the relation:

$$W_{ay} = \frac{(W_{a4} - W_{a3})}{(W_{m4} - W_{m3})} \cdot (W_{my} - W_{m3}) + W_{a3}.$$

5. A method according to claim 1 wherein a third parametric transducer is disposed in operative position relative to one of the first and second fluid compartments, wherein the substep of subjecting the first and second transducers to a pre-selected parametric value also includes subjecting the third transducer to said pre-selected parametric value, and said substep of recording in a data table the respective first and second parametric measurements further includes recording the parametric measurement of said third transducer as a result of being subjected to said pre-selected parametric value, and said sub-step of repeating further includes repeating for the first two steps for a set of pre-selected parametric values for the third transducer as well; wherein the measurements of the third parametric transducer are used as reference correction quantities; and wherein the substep of converting the operationally measured parametric values includes using two point interpolation in which the first corrected value, hereafter called $F_{ax}$, is related to the first operationally measured parametric value, hereafter called $F_{mx}$, relative to the two closest sets of recorded correction quantities, hereafter called $R_{a1}$, $F_{m1}$, and $R_{a2}$, $F_{m2}$, thereto ($R_{a1}$ and $R_{a2}$ being the reference correction quantities from the third transducer), by the relation:

$$F_{ax} = \frac{(R_{a2} - R_{a1})}{(F_{m2} - F_{m1})} \cdot (F_{mx} - F_{m1}) + R_{a1};$$

and, the second corrected parametric value, hereafter called $W_{ay}$, is related to the second operationally measured parametric value, hereafter called $W_{my}$, relative to the two closest sets of recorded correction quantities, hereafter called $R_{a3}$, $W_{m3}$, and $R_{a4}$, $W_{m4}$, thereto ($R_{a3}$ and $R_{a4}$ being the reference correction quantities from the third transducer), by the relation:

$$W_{ay} = \frac{(R_{a4} - R_{a3})}{(W_{m4} - W_{m3})} \cdot (W_{my} - W_{m3}) + R_{a3}.$$

6. A method according to claim 1 wherein the substep of converting the operationally measured parametric values includes using an added correction element, hereafter called $C_{s1}$, in which the first corrected parametric value, hereafter called $F_{ax}$, is related to the first operationally measured parametric value, hereafter called $F_{mx}$, relative to the closest set of recorded correction quantities, hereafter called $F_{m1}$ and $W_{m1}$, thereto, by the relation:

$$F_{ax} = F_{mx} - \tfrac{1}{2} C_{s1}; \text{ whereby } C_{s1} = F_{m1} - W_{m1}.$$

7. A method according to claim 6 wherein the substep of converting the operationally measured parametric values further includes using a second added correction element, hereafter called $C_{s2}$, in which the second corrected parametric value, hereafter called $W_{ay}$, is related to the second operationally measured parametric value, hereafter called $W_{my}$, relative to the closest recorded correction quantities, hereafter called $F_{m2}$ and $W_{m2}$, thereto, by the relation:

$$W_{ay} = W_{my} + \tfrac{1}{2} C_{s2}; \text{ whereby } C_{s2} = F_{m2} - W_{m2}.$$

8. A method according to claim 1 wherein a third parametric transducer is disposed in operative position relative to one of the first and second fluid containers, wherein the substep of subjecting the first and second transducers to a pre-selected parametric value also includes subjecting the third transducer to said pre-selected parametric value, and said substep of recording in a data table the respective first and second parametric measurements further includes recording the parametric measurement of said third transducer as a result of being subjected to said pre-selected parametric value, and said sub-step of repeating these first two steps further includes repeating for the first two steps for a set of pre-selected parametric values for the third transducer as well; wherein the measurements of the third parametric transducer are used as reference correction quantities; and wherein the substep of converting the operationally measured parametric values includes using an added correction quantity in which the first corrected parametric value, hereafter called $F_{ax}$, is related to the first operationally measured parametric value, hereafter called $F_{mx}$, relative to the closest recorded correction quantities, hereafter, $R_{a1}$, $F_{m1}$, thereto ($R_{a1}=R_{m1}$, being the reference correction quantities from the third transducer), by the relation:

$$F_{ax}=F_{mx}+C_{sx}; \text{ wherein } C_{sx}=R_{mx}-F_{mx}=C_{s1}=R_{m1}-F_{m1}.$$

9. A method according to claim 8 wherein the second corrected parametric value, hereafter called $W_{ay}$, is related to the second operationally measured parametric value, hereafter called $W_{my}$, relative to the closest recorded correction quantities, hereafter called $R_{a3}$, $W_{m3}$, thereto ($R_{a3}=R_{m3}$ being the reference correction quantities from the third transducer), by the relation:

$$W_{ay}=W_{my}-C_{sy}; \text{ wherein } C_{sy}=R_{my}-W_{my}=C_{s3}=R_{m3}-W_{m3}.$$

10. A method for measuring a parametric difference in a fluid system which has a first and a second flow channel separated by a semi-permeable membrane, the first fluid channel having a first parametric transducer operatively associated therewith, the second fluid channel having a second parametric transducer operatively associated therewith, the method comprising the steps of:
preliminary to actual use:
  a) subjecting the first and second transducers to a pre-selected parametric value;
  b) recording in a data table the pre-selected parametric value and the corresponding first and second parametric measurements measured by the respective first and second transducers and calling the recorded parametric value and at least one of the corresponding parametric measurements a set of correction quantities;
  c) repeating the above steps a) and b) for a set of pre-selected parametric values; and, during actual use:
  d) exposing the respective first and second transducers to respective first and second fluids in the first and second fluid channels; and
  e) calculating the parametric difference as follows:
    1) measuring the first and second operational parametric values;
    2) locating in the data table the respective sets of correction quantities closest to the respective operationally measured parametric values;
    3) using interpolation to convert the operationally measured parametric values into first and second corrected parametric quantities to find the parametric difference according to:

parametric difference=first corrected quantity−second corrected quantity.

11. A method according to claim 10 wherein the substep of using interpolation to convert the operationally measured parametric values includes using single point interpolation in which the first corrected quantity, hereafter called $F_{ax}$, is related to the first operationally measured parametric value, hereafter called $F_{mx}$, relative to the closest recorded set of correction quantities, hereafter called $F_{a1}$, $F_{m1}$, thereto, by the relation:

$$F_{ax} = F_{mx} \cdot \frac{(F_{a1})}{(F_{m1})};$$

and, the second corrected parametric quantity, hereafter called $W_{ay}$, is related to the second operationally measured parametric value, hereafter called $W_{my}$, relative to the closest recorded set of correction quantities, hereafter called $W_{a2}$, $W_{m2}$, thereto, by the relation:

$$W_{ay} = W_{my} \cdot \frac{(W_{a2})}{(W_{m2})}.$$

12. A method according to claim 10 wherein the substep of using interpolation to convert the operationally measured parametric values includes using two point interpolation in which the first corrected parametric quantity, hereafter called $F_{ax}$, is related to the first operationally measured parametric value, hereafter called $F_{mx}$, relative to the two closest recorded sets of correction quantities, hereafter called $F_{a1}$, $F_{m1}$, and $F_{a2}$, $F_{m2}$, thereto, by the relation:

$$F_{ax} = F_{mx} \cdot \frac{(F_{a2} - F_{a1})}{(F_{m2} - F_{m1})};$$

and, the second corrected parametric quantity, hereafter called $W_{ay}$, is related to the second operationally measured parametric value, hereafter called $W_{my}$, relative to the two closest recorded sets of correction quantities, hereafter called $W_{a3}$, $W_{m3}$, and $W_{a4}$, $W_{m4}$, thereto, by the relation:

$$W_{ay} = W_{my} \cdot \frac{(W_{a4} - W_{a3})}{(W_{m4} - W_{m3})}.$$

13. A method according to claim 10 wherein the substep of using interpolation to convert the operationally measured parametric values includes using two point interpolation in which the first corrected parametric quantity, hereafter called $F_{ax}$, is related to the first operationally measured parametric value, hereafter called $F_{mx}$, relative to the two closest recorded sets of correction quantities, hereafter called $F_{a1}$, $F_{m1}$, and $F_{a2}$, $F_{m2}$, thereto, by the relation:

$$F_{ax} = \frac{(F_{a2} - F_{a1})}{(F_{m2} - F_{m1})} \cdot (F_{mx} - F_{m1}) + F_{a1};$$

and, the second corrected parametric quantity, hereafter called $W_{ay}$, is related to the second operationally measured parametric value, hereafter called $W_{my}$, relative to the two closest recorded sets of correction quantities, hereafter called $W_{a3}$, $W_{m3}$, and $W_{a4}$, $W_{m4}$, thereto, by the relation:

$$W_{ay} = \frac{(W_{a4} - W_{a3})}{(W_{m4} - W_{m3})} \cdot (W_{my} - W_{m3}) + W_{a3}.$$

14. A method according to claim 10 wherein a third parametric transducer is disposed in operative position relative to one of the first and second fluid channels, wherein the substep of subjecting the first and second transducers to a pre-selected parametric value also includes subjecting the third transducer to said pre-selected parametric value, and said substep of recording in a data table the respective first and second parametric measurements further includes recording the parametric measurement of said third transducer as a result of being subjected to said pre-selected parametric value, and said sub-step of repeating the first two steps further includes repeating the first two steps of subjecting and recording for the set of pre-selected parametric values for the third transducer as well; wherein the measurements of the third parametric transducer are used as reference correction quantities; and wherein the substep of using interpolation to convert the operationally measured parametric values includes using two point interpolation in which the first corrected quantity, hereafter called $F_{ax}$, is related to the first operationally measured parametric value, hereafter called $F_{mx}$, relative to the two closest sets of recorded correction quantities, hereafter called $R_{a1}, F_{m1}$, and $R_{a2}, F_{m2}$, thereto ($R_{a1}$ and $R_{a2}$ being the reference correction quantities from the third transducer), by the relation:

$$F_{ax} = \frac{(R_{a2} - R_{a1})}{(F_{m2} - F_{m1})} \cdot (F_{mx} - F_{m1}) + R_{a1};$$

and, the second corrected parametric quantity, hereafter called $W_{ay}$, is related to the second operationally measured parametric value, hereafter called $W_{my}$, relative to the two closest sets of recorded correction quantities, hereafter called $R_{a3}, W_{m3}$, and $R_{a4}, W_{m4}$, thereto ($R_{a3}$ and $R_{a4}$ being the reference correction quantities from the third transducer), by the relation:

$$W_{ay} = \frac{(R_{a4} - R_{a3})}{(W_{m4} - W_{m3})} \cdot (W_{my} - W_{m3}) + R_{a3}.$$

15. A method according to claim 14 wherein the substep of using interpolation includes using the third transducer measurements as reference correction quantities in a two point interpolation such that:

$F_{m1}$=the closest lower correction quantity associated with $F_{mx}$;

$F_{m2}$=the closest upper correction quantity associated with $F_{mx}$;

$R_{m1}$=the third transducer correction quantity that corresponds to $F_{m1}$;

$R_{m2}$=the third transducer correction quantity that corresponds to $F_{m2}$; and by linear interpolation, $$F_{ax} = \frac{R_{m2} - R_{m1}}{F_{m2} - F_{m1}} \cdot (F_{mx} - F_{m1}) + R_{m1}; \text{ and,}$$

$W_{m3}$=the closest lower correction quantity associated with $W_{my}$;

$W_{m4}$=the closest upper correction quantity associated with $W_{my}$;

$R_{m3}$=the third transducer correction quantity that corresponds to $W_{m3}$;

$R_{m4}$=the third transducer correction quantity that corresponds to $W_{m4}$; and by linear interpolation, $$W_{ay} = \frac{R_{m4} - R_{m3}}{W_{m4} - W_{m3}} \cdot (W_{my} - W_{m3}) + R_{m3}.$$

16. A method for measuring a parametric difference in a fluid system which has a first and a second flow channel separated by a semi-permeable membrane, the first fluid channel having a first parametric transducer operatively associated therewith, the second fluid channel having a second parametric transducer operatively associated therewith, the method comprising the steps of:

preliminary to actual use:

a) subjecting the first and second transducers to a pre-selected parametric value;

b) recording in a data table the respective first and second parametric measurements measured by the first and second transducers and calling these parametric measurements a set of correction quantities;

c) repeating the above steps a) and b) for a set of pre-selected parametric values; and, during actual use:

d) exposing the respective first and second transducers to respective first and second fluids in the first and second fluid channels; and e) calculating the parametric difference as follows:
1) measuring the first and second operational parametric values;
2) locating in the data table the first and second sets of correction quantities closest to the respective operationally measured parametric values;
3) using the located first and second sets of correction quantities to convert the operationally measured parametric values into first and second corrected parametric quantities to find the parametric difference according to:

parametric difference=first corrected quantity−second corrected quantity.

17. A method according to claim 16 wherein the substep of converting the operationally measured parametric values includes using an added correction element, hereafter called $C_{s1}$, in which the first corrected parametric quantity, hereafter called $F_{ax}$, is related to the first operationally measured parametric value, hereafter called $F_{mx}$, relative to the closest set of recorded correction quantities, hereafter called $F_{m1}$ and $W_{m1}$, thereto, by the relation:

$F_{ax}=F_{mx}-\frac{1}{2}C_{s1}$; whereby $C_{s1}=F_{m1}-W_{m1}$.

18. A method according to claim 17 wherein the substep of converting the operationally measured parametric values further includes using a second added correction element, hereafter called $C_{s2}$, in which the second corrected parametric quantity, hereafter called $W_{ay}$, is related to the second operationally measured parametric value, hereafter called $W_{my}$, relative to the closest recorded set of correction quantities, hereafter called $F_{m2}$, and $W_{m2}$, thereto, by the relation:

$W_{ay}=W_{my}+\frac{1}{2}C_{s2}$; whereby $C_{s2}=F_{m2}-W_{m2}$.

19. A method according to claim 16 wherein a third parametric transducer is disposed in operative position relative to one of the first and second fluid channels, wherein the substep of subjecting the first and second transducers to a pre-selected parametric value also includes subjecting the third transducer to said pre-selected parametric value, and said substep of recording in a data table the respective first and second parametric measurements further includes recording the parametric measurement of said third transducer as a result of being subjected to said pre-selected parametric value, and said sub-step of repeating these first two steps further includes repeating for the first two steps for a set of pre-selected parametric values for the third transducer as well; wherein the measurements of the third parametric transducer are used as reference correction quantities; and wherein the substep of converting the operationally measured parametric values includes using an added correction element in which the first corrected parametric quantity, hereafter called $F_{ax}$, is related to the first operationally measured parametric value, hereafter called $F_{mx}$, relative to the closest recorded correction quantities, hereafter, $R_{a1}$, $F_{m1}$, thereto ($R_{a1}=R_{m1}$ being the reference correction quantities from the third transducer), by the relation:

$$F_{ax}=F_{mx}+C_{sx}; \text{ wherein } C_{sx}=R_{mx}-F_{mx}=C_{s1}=R_{m1}-F_{m1}.$$

20. A method according to claim 19 wherein the second corrected parametric quantity, hereafter called $W_{ay}$, is related to the second operationally measured parametric value, hereafter called $W_{my}$, relative to the two closest sets of recorded correction quantities, hereafter called $R_{a3}$, $W_{m3}$, thereto ($R_{a3}=R_{m3}$ being the reference correction quantities from the third transducer), by the relation:

$$W_{ay}=W_{my}-C_{sy}; \text{ wherein } C_{sy}=R_{my}-W_{my}=C_{s3}=R_{m3}-W_{m3}.$$

21. A method for measuring a trans-membrane pressure (TMP) in a system which has a first and a second flow channel separated by a semi-permeable membrane, the first flow channel having a filter pressure transducer operatively associated therewith on the upstream side of the first flow channel and a return pressure transducer operatively associated therewith on the downstream side of the first flow channel, the second flow channel having an effluent pressure transducer operatively associated therewith, the filter, effluent and return pressure transducers each having a transducer side and an opposing fluid side, the transducer sides being adapted to be exposed to controlled pressurizations through connection to a compressed fluid circuit which includes a compressed fluid source, the method comprising the steps of:

a) opening exposure of the filter, effluent, and return transducers to communication with the compressed fluid circuit;

b) using the return transducer as the standard, applying a controlled pressurization to the transducer sides of the filter, effluent and return transducers to minus 50 mmHg.;

c) allowing the applied pressurization to stabilize;

d) recording in a data table the measured filter pressure value, measured effluent pressure value, and measured return pressure value; calling these pressure values correction pressure quantities;

e) repeating the above steps a) through d) for applied pressurizations of 0, +50, +100, +150, +200, +250, +300, +350, +400, +450 mmHg.;

f) closing off communication of the transducers with the compressed fluid circuit;

the g) exposing the respective transducers to respective first and second fluid flows in the first and second fluid flow channels; and h) calculating the trans-membrane pressure, hereafter referred to as the TMP, as follows:
1) measuring an operational filter pressure value;
2) locating in the data table the two filter correction pressure quantities closest to the measured operational filter pressure value;
3) using interpolation to convert the measured operational filter pressure value into a Corrected Filter Pressure according to:
$F_{lx}$ the closest recorded lower filter correction pressure quantity;
$F_u$=the closest recorded upper filter correction pressure quantity;
$R_{Fl}$=the return correction pressure quantity that corresponds to the lower filter correction pressure quantity;
$R_{Fu}$=the return correction pressure quantity that corresponds to the upper filter correction pressure quantity; and, Corrected Filter Pressure =

$$\frac{R_{Fu}-R_{Fl}}{F_u-F_l} \cdot (\text{Measured Filter Pressure} - F_l) + R_{Fl};$$

and
4) measuring an operational effluent pressure value;
5) locating in the data table the two effluent correction pressure quantities closest to the measured operational effluent pressure value;
6) using interpolation to convert the measured operational effluent pressure value into a Corrected Effluent Pressure according to:
$E_l$=the closest recorded lower effluent correction pressure quantity;
$E_u$=the closest recorded upper effluent correction pressure quantity;
$R_{El}$=the return correction pressure quantity that corresponds to the lower effluent correction pressure quantity;
$R_{Eu}$=the return correction pressure quantity that corresponds to the upper effluent correction pressure quantity; and, Corrected Effluent Pressure =

$$\frac{R_{Eu}-R_{El}}{E_u-E_l} \cdot (\text{Measured Effluent Pressure} - E_l) + R_{El};$$

and
7) using the Corrected Filter Pressure and the Corrected Effluent Pressure to calculate the TMP as follows:

TMP=Corrected Filter Pressure−Corrected Effluent Pressure.

22. A method for measuring a trans-membrane pressure (TMP) in a system which has a first and a second flow channel separated by a semipermeable membrane, the first flow channel having a filter pressure transducer operatively associated therewith on the upstream side of the first flow channel and a return pressure transducer operatively associated therewith on the downstream side of the first flow channel, the second flow channel having an effluent pressure transducer operatively associated therewith, the filter, effluent and return pressure transducers each having an air side and an opposing measured fluid side, the air sides being adapted to be exposed to controlled pressurizations through connection to a compressed air circuit which includes a compressed air source, the method comprising the steps of:

a) opening exposure of the filter, effluent, and return transducers to communication with the compressed air circuit;
b) using the return transducer as the standard, applying a pressurization to the air sides of the filter, effluent and return transducers to minus 50 mmHg.;
c) allowing the applied pressurization to stabilize;
d) recording in a data table the measured filter pressure value, measured effluent pressure value, and measured return pressure value; calling these pressure values correction pressure quantities;
e) repeating the above steps a) through d) for air pressures of 0, +50, +100, +150, +200, +250, +300, +350, +400, +450 mmHg.;
f) closing off communication of the transducers with the compressed fluid circuit;
g) exposing the transducers to respective first and second fluid flows in the first and second fluid flow channels; and
h) calculating the trans-membrane pressure, hereafter the TMP, as follows:
  1) measuring an operational filter pressure value;
  2) locating in the data table the filter correction quantities closest to the operationally measured filter pressure value;
  3) using an added correction element to convert the measured filter pressure value into a Corrected Filter Pressure according to:
    $F_{mx}$=the operationally measured filter pressure value;
    $F_{m1}$=the closest recorded filter correction pressure quantity;
    $R_{mx}$=the return pressure value that corresponds to the operationally measured filter pressure value;
    $R_{m1}$=the return pressure correction quantity that corresponds to the closest recorded filter correction pressure quantity; and,
    Corrected Filter Pressure=; and =$F_{mx}+C_{sx}$; wherein $C_{sx}=R_{mx}-F_{mx}$;

and as a substitution $R_{mx}=R_{m1}$;
  4) measuring an operational effluent pressure value;
  5) locating in the data table the effluent correction quantities closest to the operationally measured effluent pressure value;
  6) using an added correction element to convert the measured effluent pressure value into a Corrected Effluent Pressure according to:
    $E_{my}$=the operationally measured effluent correction pressure value;
    $E_{m2}$=the closest recorded effluent correction pressure quantity;
    $R_{my}$=the return pressure value that corresponds to the operationally measured effluent pressure value;
    $R_{m2}$=the return pressure correction quantity that corresponds to the closest recorded effluent correction pressure quantity; and
    Corrected Effluent Pressure=

$E_{my}+C_{sy}$; wherein $C_{sy}=R_{my}-E_{my}$;

and as a substitution $R_{my}=R_{m2}$; and
  7) using the Corrected Filter Pressure and the Corrected Effluent Pressure to calculate the TMP as follows:

TMP=Corrected Filter Pressure−Corrected Effluent Pressure.

* * * * *